US011633572B2

(12) United States Patent
Gaasbeek et al.

(10) Patent No.: US 11,633,572 B2
(45) Date of Patent: Apr. 25, 2023

(54) OVER-ACTUATED HYSTERETIC SYSTEMS AND METHODS FOR CONTROL OF SAME

(71) Applicant: Eindhoven Medical Robotics B.V., Eindhoven (NL)

(72) Inventors: Rolf Iwan Gaasbeek, Nuenen (NL); Petrus Johannes Maria Aerts, Aalst-Waalre (NL)

(73) Assignee: Eindhoven Medical Robotics B.V., Eindhoven (NL)

( * ) Notice: Subject to any disclaimer, the term of this patent is extended or adjusted under 35 U.S.C. 154(b) by 632 days.

(21) Appl. No.: 16/627,946

(22) PCT Filed: Jul. 3, 2018

(86) PCT No.: PCT/EP2018/067984
§ 371 (c)(1),
(2) Date: Dec. 31, 2019

(87) PCT Pub. No.: WO2019/007977
PCT Pub. Date: Jan. 10, 2019

(65) Prior Publication Data
US 2021/0154434 A1    May 27, 2021

Related U.S. Application Data

(60) Provisional application No. 62/528,389, filed on Jul. 3, 2017.

(51) Int. Cl.
*A61M 25/01*    (2006.01)
*A61B 1/005*    (2006.01)
*F03G 7/06*    (2006.01)

(52) U.S. Cl.
CPC ......... *A61M 25/0158* (2013.01); *F03G 7/065* (2013.01); *F03G 7/0614* (2021.08); *A61B 1/0058* (2013.01); *A61M 2205/0266* (2013.01)

(58) Field of Classification Search
CPC ...... A61M 25/0158; A61M 2205/0266; A61B 1/0058; A61B 1/00006; F03G 7/0614
See application file for complete search history.

(56) References Cited

U.S. PATENT DOCUMENTS

| | | | |
|---|---|---|---|
| 5,624,380 A | 4/1997 | Takayama et al. | |
| 5,897,488 A * | 4/1999 | Ueda | B25J 18/06 600/151 |

(Continued)

FOREIGN PATENT DOCUMENTS

| | | |
|---|---|---|
| CN | 104678529 A | 6/2015 |
| CN | 104363821 B | 3/2017 |

(Continued)

OTHER PUBLICATIONS

Naser, Fuad Mohammad, M., & Ikhouane, F. (2013). Characterization of the hysteresis Duhem model. IFAC Proceedings Volumes, 46(12), 29-34. https://doi.org/10.3182/20130703-3-fr-4039.00008 (Year: 2013).*

(Continued)

*Primary Examiner* — Tasnim Mehjabin Ahmed
(74) *Attorney, Agent, or Firm* — Suiter Swantz pc llo

(57) ABSTRACT

An over-actuated system [304], such as a catheter, having shape memory alloy (SMA) hysteretic wire actuators is controlled using a controller [300, 302] that generates a control signal [310] based on a temperature model that takes into account physical limitations of the SMA hysteretic wire actuators, and based on a hysteresis model (e.g., the Duhem model) that describes hysteresis behavior of the SMA hysteretic wire actuators. The controller preferably includes a feedback controller [302] and a reference governor [300] that generates a smart reference signal [308] from a reference signal [306] representing a desired value of an output of the system. The smart reference signal preferably minimizes an error between the reference signal and an achiev- (Continued)

able output, and the control signal preferably is generated based on the smart reference signal.

15 Claims, 20 Drawing Sheets

(56) References Cited

U.S. PATENT DOCUMENTS

| | | | |
|---|---|---|---|
| 7,188,473 | B1 | 3/2007 | Asada et al. |
| 8,961,433 | B2 | 2/2015 | Patel et al. |
| 2005/0006009 | A1 | 1/2005 | Esashi et al. |
| 2007/0239138 | A1* | 10/2007 | Lawrence .............. A61B 1/012 |
| | | | 604/95.05 |
| 2009/0099551 | A1 | 4/2009 | Tung et al. |
| 2013/0296885 | A1 | 11/2013 | Desai et al. |

FOREIGN PATENT DOCUMENTS

| | | |
|---|---|---|
| CN | 104204935 B | 5/2017 |
| CN | 104267820 B | 7/2017 |
| CN | 104982028 B | 8/2018 |
| WO | 2017098249 A1 | 6/2017 |

OTHER PUBLICATIONS

Zakerzadeh, M. R., & Sayyaadi, H. (2013). Precise position control of shape memory alloy actuator using inverse hysteresis model and model reference Adaptive Control System. Mechatronics, 23(8), 1150-1162. https://doi.org/10.1016/j.mechatronics.2013.10.001 (Year: 2013).*

* cited by examiner

*Fig. 1A*
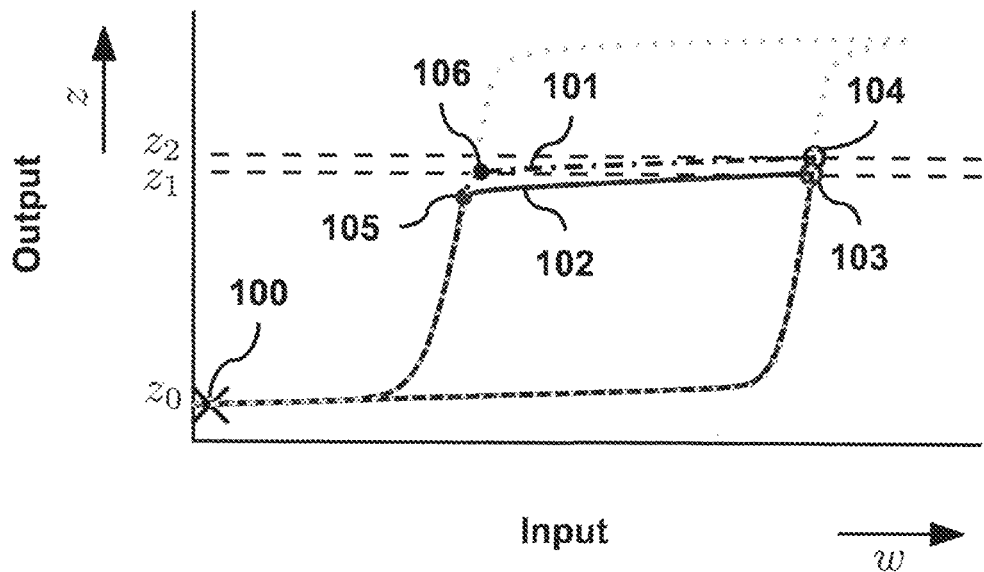
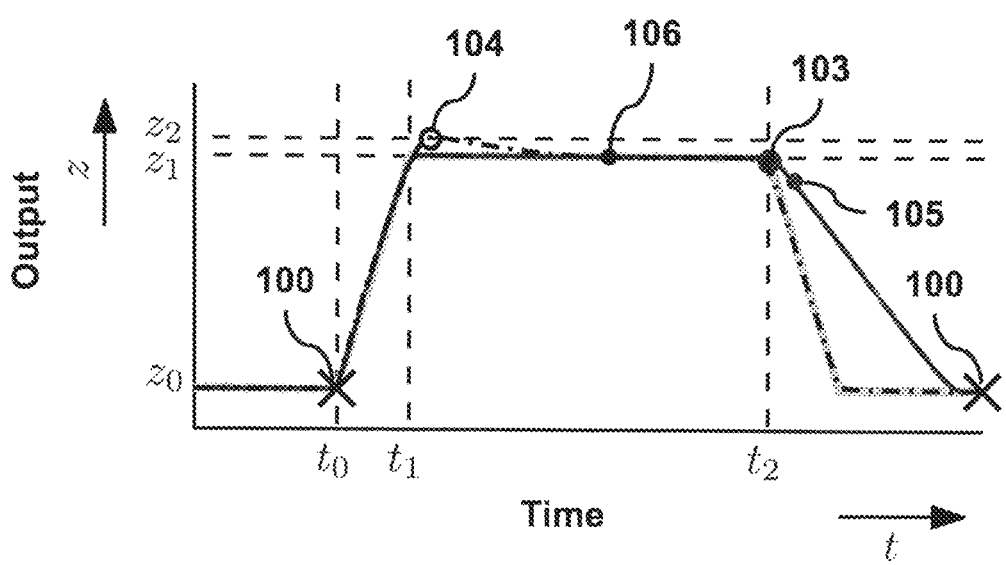
*Fig. 1B*

OVER-ACTUATED HYSTERETIC SYSTEMS AND METHODS FOR CONTROL OF SAME

FIELD OF THE INVENTION

The present invention relates generally to hysteretic systems and methods for their control. More specifically, it relates to devices using shape memory alloy actuators and methods for their control.

BACKGROUND OF THE INVENTION

In hysteretic systems several inherently different states can result in identical output, i.e., there exists a multi-valued map between input and output of a hysteretic system. This nonlinear behavior prevents direct application of linear control techniques. As a result, conventional wisdom views hysteresis as an effect to be avoided. Conventionally, control structures are incorporated that eliminate or neglect the hysteretic effect, and by that, simplify control design and analysis. Several control structures have been proposed to deal with hysteresis. For instance by making the controller robust for the "unwanted" hysteresis (e.g., sliding mode, adaptive control), by eliminating the "unwanted" hysteresis (e.g., inverse-based control), or by ignoring the existence of the 'unwanted' hysteretic behavior (linearization). These approaches, however, have various drawbacks, especially for systems where fast response times are desired.

BRIEF SUMMARY OF THE INVENTION

In contrast with known approaches to controlling hysteretic systems, where hysteretic effects are avoided or eliminated, the inventors have discovered an approach in which the multi-valued mapping of a hysteretic system is actively exploited. Especially on systems where the rate of change of the input is limited, e.g., temperature controlled shape memory alloy actuators, the framework results in significant tracking improvements, and hence accurate steering capabilities. The methodology is demonstrated with experiments on an shape memory alloy actuator and in simulation on a robotic catheter system. More generally, the techniques of the invention apply to bendable tubular devices, such as endoscopes.

In one aspect, the invention provides a method for controlling an over-actuated system having shape memory alloy (SMA) hysteretic wire actuators. The over-actuated system may be, for example, a catheter. The method includes generating by a controller a control signal, wherein the control signal is generated based on a temperature model that takes into account physical limitations of the SMA hysteretic wire actuators, and based on a hysteresis model (e.g., the Duhem model) that describes hysteresis behavior of the SMA hysteretic wire actuators; inputting to the SMA hysteretic wire actuators the control signal, wherein the SMA hysteretic wire actuators comprise at least three SMA wire actuators; and changing displacement states of the SMA hysteretic wire actuators based on the control signal, such that a tip of the over-actuated system moves with a number of degrees of freedom less than the number of SMA wire actuators. For example, in some implementations, the tip of the over-actuated system moves with two degrees of freedom, and the number of SMA wire actuators is at least three.

Preferably, the controller includes a feedback controller that tracks a reference signal representing a desired value of an output of the SMA hysteretic wire actuators. Preferably, the controller comprises a reference governor that generates a smart reference signal from a reference signal representing a desired value of an output of the SMA hysteretic wire actuators. The smart reference signal preferably minimizes an error between the reference signal and an achievable output, and the control signal preferably is generated based on the smart reference signal. The reference governor preferably is dependent on the hysteresis model and an inverse hysteresis model.

In another aspect, the invention provides an over-actuated device, such as a catheter. The device includes a bendable tube comprising at least three shape memory alloy (SMA) hysteretic wire actuators having displacement states that change in response to a control signal such that a tip of the over-actuated system moves with a number of degrees of freedom less than the number of SMA wire actuators. For example, in one implementation, the tip of the over-actuated system moves with two degrees of freedom, and the number of SMA wire actuators is at least three. The device also includes a controller connected to the bendable tube, wherein the controller generates a control signal and inputs the control signal to the SMA hysteretic wire actuators, wherein the control signal is generated by the controller based on a temperature model that takes into account physical limitations of the SMA hysteretic wire actuators, and based on a hysteresis model (e.g., the Duhem model) that describes hysteresis behavior of the SMA hysteretic wire actuators.

The controller preferably comprises a feedback controller that tracks a reference signal representing a desired value of an output of the SMA hysteretic wire actuators. The controller preferably comprises a reference governor that generates a smart reference signal from a reference signal representing a desired value of an output of the SMA hysteretic wire actuators.

BRIEF DESCRIPTION OF THE SEVERAL VIEWS OF THE DRAWINGS

FIG. 1A and FIG. 1B are graphs of reference signals with respect to input and time, respectively, for a hysteretic system. The solid line corresponds to a hypothetical reference and response to the system due to an arbitrary feedback controller. By taking into account limitations in $\dot{w}$, a response according to embodiments of the invention (dash-dotted) exploits the hysteresis loop (by making an overshoot) and by that reaches a significantly lower value of w before a reverse movement takes place (after $t_2$). As a consequence, improved tracking accuracy of the reference signal is obtained after $t_2$.

DETAILED DESCRIPTION OF THE INVENTION

Figure 2:
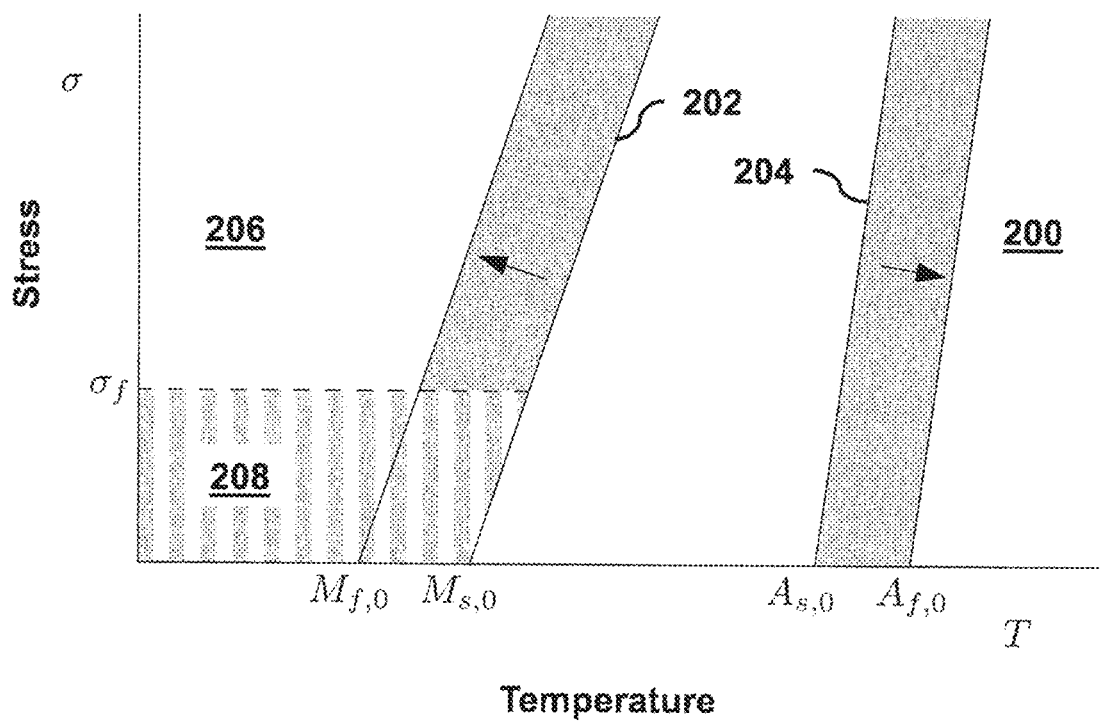
FIG. 2 is a phase diagram of stress vs. temperature illustrating the dominant transitions in crystallographic structure of a SMA wire.

According to the approach of the present invention, hysteresis should not be considered an "unwanted" difficulty, but rather an opportunity to increase performance.

An example hysteresis loop is depicted in FIG. 1A, with the manipulated input w on the horizontal axis and output z on the vertical axis. In this case the system is in state 100 initially, for increasing input the solid trajectory 102 is followed. Upon decreasing of the input, e.g., from upon state 103, the output stays almost constant up to state 105. Upon further decreasing of the input, the output is decreased until the system is back in state 100.

In FIG. 1B, a reference trajectory is provided. The system output is brought to $z_1$ ($t_0$ till $t_1$), after which it should return to the initial state 100 (from upon $t_2$). In case of classic feedback control, the input is increased to state 103. If afterwards the reference decreases, the input has to decrease significantly. Due to physical limitations (limited rate of input change) the system is unable to follow the reference; resulting in the solid output. However, if the system moves from state 103 to state 104 in $t_1 \le t \le t_2$, the system is able to follow the reference (the dash-dotted output 101). Hence, if the limitations and dynamics of the system are known, the hysteresis effect can be exploited to allow for improved tracking. Note that an error is introduced at around $t=t_1$. Later it is shown that this is not the case for over-actuated systems (more actuators than degrees of freedom).

In order to exploit the hysteresis in an optimal sense, a model-based framework is proposed. One of such approaches is to use a Model Predictive Control (MPC). Considering the typically switching non-linear nature of hysteresis models, as well as the debate on model accuracy, implementation and stability proofs are challenging for MPC frameworks. Alternatively, the reference is altered instead of the control input, as the output signals are not used, this cannot destabilize the system. The latter is known as a reference governor.

The approach of the present invention is to make use of the multivalued character of the hysteresis to avoid limitations of input constraints. This principle is demonstrated by a designed reference governor that manipulates the reference in such a way that the system takes advantage of the hysteresis effect, taking into consideration constraints of the system. As the methodology alters the reference signal without using the output, stability is not affected.

One of the more challenging type of hysteresis is the hysteretic behavior of shape memory alloy (SMA) actuated systems. Compared to other active materials SMA has significantly higher specific strain and force, making it an ideal candidate for micro-actuators. To show efficacy of the proposed reference governor, the method is applied on a 1D SMA actuated test set-up. Additionally, simulation results are shown for an SMA-actuated catheter system. It is shown that over-actuated systems are preferable for increasing overall tracking performance.

SMA is a material that changes its crystallographic structure by stress- and/or temperature variations. This can be schematically illustrated in phase diagrams. Embodiments of the present invention preferably employ actuators equipped with NiTiNol wires (150 μm-diameter Flexinol™ wire of Dynalloy Inc.). In these wires, three crystallographic structures can be present; detwinned martensite, twinned martensite and austenite.

The phase diagram corresponding with the SMA wires is shown in FIG. 2. At relatively high temperatures in region 200, the material is in Austenite state. When temperature is decreased and the SMA passes through transition region 202, the material transforms to detwinned martensite in region 206. However, upon heating, the reverse transformation occurs at a significantly higher temperature in region 204. The arrows in the transition regions 202, 204 indicate the direction of the rate of change of stress/temperature in order for transformation to occur. In the striped region 208 twinned martensite can be present. In preferred embodiments, the stresses will be above $\sigma_f$. Hence, only detwinned martensite and austenite will occur. The fraction of detwinned martensite in the material is denoted $0 \leq \xi_d \leq 1$ (hence, the fraction of non-detwinned material is $\xi_n = 1 - \xi_d$).

When imposing a transition from detwinned martensite and back, a significant strain effect is observed; the working principle of SMA actuators. The output z is a scaled displacement, which is directly related to strain of the wire. As a consequence, the large strain effect can be clearly seen in FIG. 1A, the dotted lines denote the outer loops (full transition), the solid line corresponds with an inner loop (partial transformation). The manipulated input w is temperature (or, equivalently, the applied current that heats the SMA), as the transition to austenite occurs at a higher temperature as the transition back to martensite (also visible in FIG. 2). As a consequence; hysteresis is present in the input-output relation.

In the SMA actuators used in embodiments of the invention, preferably a SMA wire is pre-stressed by a bias force. Then, by manipulating the temperature of the wire, an actuating effect is observed. Heating is obtained by applying a current to the wire (Joule heating), cooling occurs by natural convection. The rate of cooling is especially limited, which is a significant problem for other approaches to control of SMA actuators.

To exploit the hysteresis effect, the reference is manipulated to allow more sophisticated routes through the hysteresis cycle using a reference governor (RG) framework.

Figure 3:
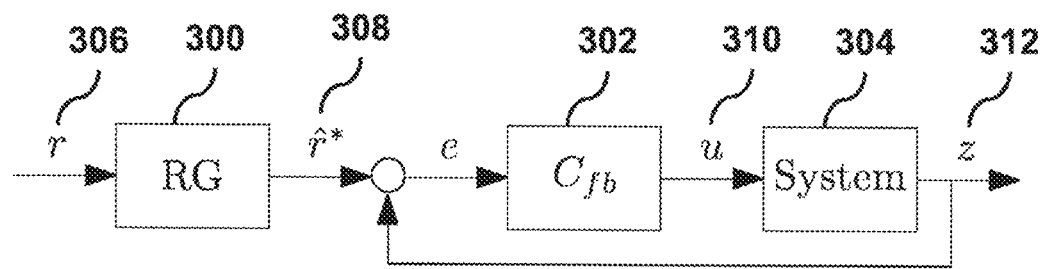
FIG. 3 is a schematic representation of a controller including a reference governor (RG) used to manipulate the reference signal before entering a control loop.

FIG. 3 shows the RG as the block RG 300. Furthermore, a relatively straightforward feedback controller $C_{fb}$ 302 is used. The RG generates from reference signal 306 a smart reference 308 that takes into account physical constraints of the system 304. The feedback controller 302 can accurately track such reference. Feedback controller 302 generates control signal 310 (e.g., current) that is input into system 304 to produce system output 312 (e.g., movement of catheter tip).

The manipulated state is denoted w, which is not necessarily the same as the input to the system (e.g., for SMA actuators, the input is current for Joule heating u=I and the manipulated state is temperature w=T). In order to track the reference, a certain w is used. However, physical rate limitations are present:

$$\dot{w}_{min} < \dot{w} < \dot{w}_{max}, \quad (1)$$

where $\dot{w}_{min}$ is the minimal rate of change in w that can be achieved (for SMA actuators, the minimum rate of temperature is normally a consequence of the convective cooling). Likewise, $\dot{w}_{max}$ denotes the maximum rate of change in w (for SMA actuators; the power-limitation of the current amplifier).

Figure 4:
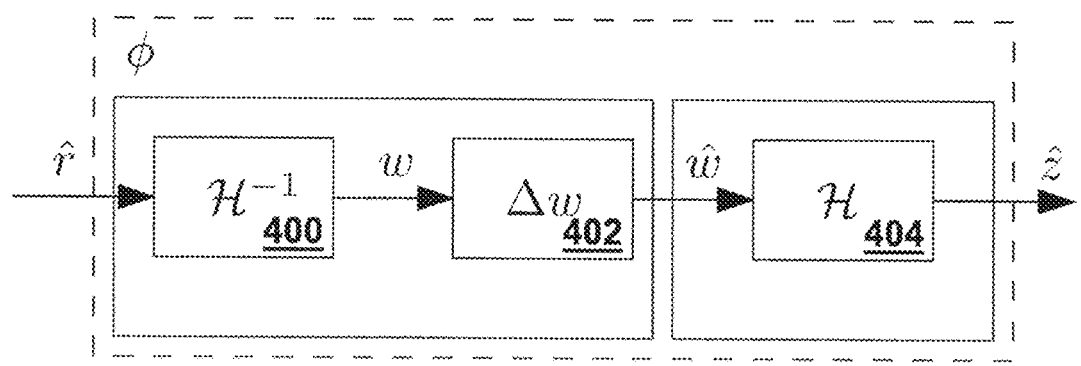
FIG. 4 is a schematic illustration of a procedure to determine the achievable output $\hat{z}$ for a certain reference $\hat{r}$. An inverse model of the plant ($\mathcal{H}^{-1}$) is applied to the considered reference $\hat{r}$ in order to obtain a required input w, bounds on rate of change $\dot{w}$ are implemented to find an achievable input $\hat{w}$, and the achievable input is applied to the model to find a feasible output $\hat{z}$.

FIG. 4 schematically depicts a procedure according to an embodiment of the invention to determine the achievable output $\hat{z}$, using a certain reference $\hat{r}$. The hysteretic system is denoted $\mathcal{H}$ 404. First $\hat{r}$ is passed through the inverse $\mathcal{H}^{-1}$ 400 of the hysteretic system, whose output is a manipulation state w. Then limitations of $\dot{w}$ are taken into account in block 402, resulting in a manipulated $\hat{w}$ that obeys Eq. 1. This feasible $\hat{w}$ is applied to the system model $\mathcal{H}$, ultimately resulting in an achievable output $\hat{z} = \phi(\hat{r})$. By modifying $\hat{r}$, the actual output can become closer to the initial reference. Hence, in the RG the error $(r - \hat{z})$ is minimized. This is achieved by minimizing the following cost function:

$$J_{RG} = \min_{\hat{r}} \sum_{k=1}^{N-1} (r - \phi(\hat{r}))^2, \quad (2)$$

where N is the number of data-points. Note that r can be used as an initial guess for $\hat{r}$. The optimal $\hat{r}^*$ is applied on the system enforcing it to exploit the multi-valued hysteretic behavior. The RG is applied offline, and therefore, the complete trajectory is assumed to be known beforehand. If the temperature model (and hence, $\Delta w$) is accurate, no physical input constraints are violated. Hence, the methodology is robust for errors in the (typical least accurate) hysteresis model.

Figure 5:
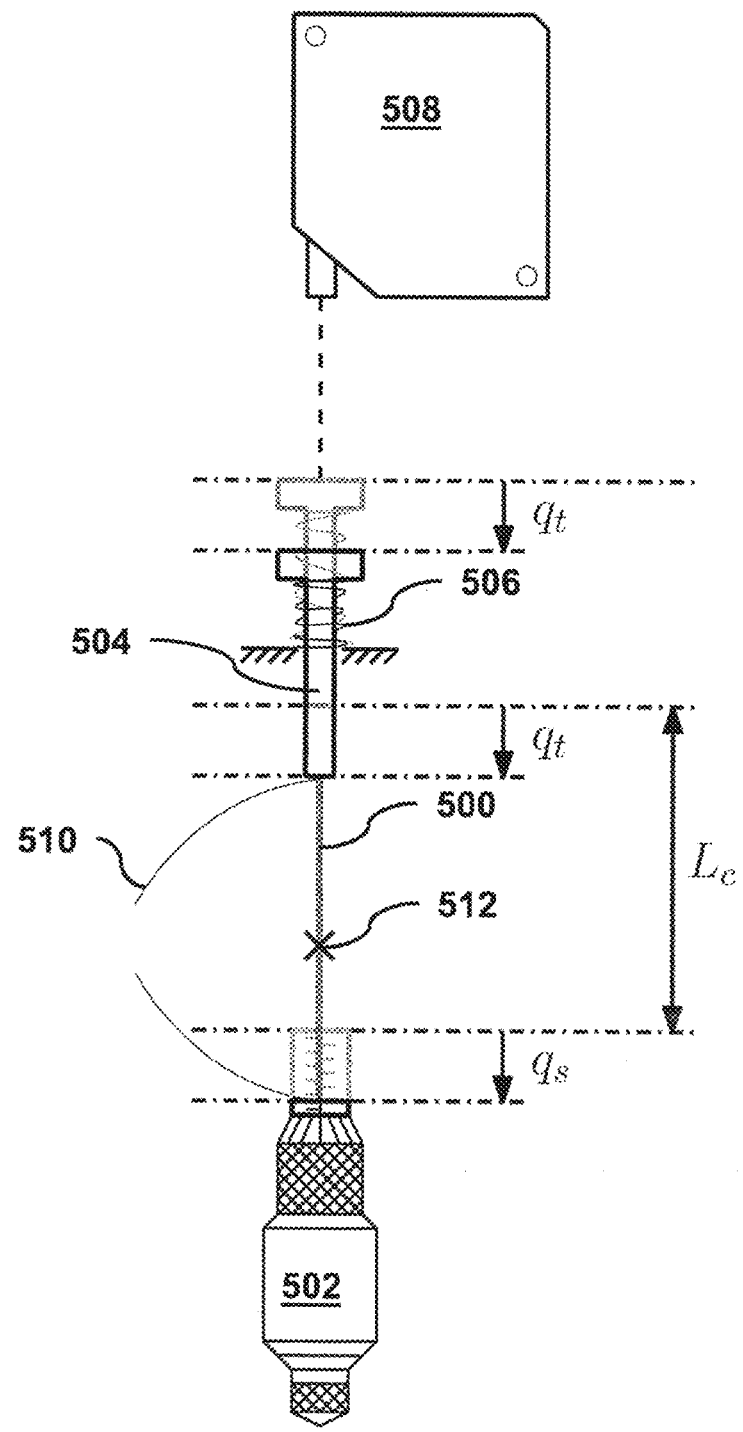
FIG. 5 is a schematic illustration of an experimental bias-spring SMA-actuator set-up used to test the control method.

The measurement data described below is obtained by a bias-spring actuator set-up (the bias force is generated by a spring). In the bias-spring actuator set-up, schematically depicted in FIG. 5, a Flexinol™ (Dynalloy Inc.) SMA wire 500 is vertically strung between a microspindle 502 and a pin 504 attached to a spring 506. The spring provides a bias force to the wire, the microspindle is used to regulate this bias-forced and remains untouched during experiment.

The position of the tip of the top pin $q_t$ is measured contact-less by laser sensor 508 and is directly related to the length of the wire. This position is fed back to the feedback controller. By applying a current through the SMA wire 500 using copper wire 510, the SMA wire heats up and contracts, resulting in a downwards movement of the top pin 504. By cooling of the wire 500 (by natural convection to air), an opposite movement of the top pin 504 is observed. Thermocouple 512 measures the temperature of the SMA wire 500. During the experiments the micro-spindle setting $q_s$ is chosen such that the stresses during the experiment are above $\sigma_f$ in FIG. 2. Thus, only detwinned martensite and austenite can occur.

The reference governor is dependent on both a hysteresis model as well as an inverse hysteresis model.

The hysteresis model is used in the control framework, hence, it should be computationally efficient, accurate and invertible. Three modeling strategies are used in modeling of SMA hysteresis:

Physical models are derived from conservations laws. Free energy is solved on a microscopic level, by assuming homogeneity throughout the materia. This can be related to macroscopic behavior of the SMA wire. An example of such models is the Müller-Achenbach-Seelecke model. As the crystallographic changes in the material do not occur homogeneously throughout the material, physical models have limited accuracy on a macroscopic level. Workarounds to improve accuracy have been proposed, e.g., based on an empirically found "certain distribution" and applying a stochastic homogenization procedure. One could argue if this knowledge adds much value from a control perspective, when compared to other model type which (experimentally) estimate a macroscopic behavior directly. Additionally, an important practical problem with these models is that some of the defined parameters in the models are not measurable with standard characterization tests.

Empirical physics-based models are models that rely on a constitutive equation. The components of the equation are dominantly related back to physical properties of the system. However, the fraction of transformed material is estimated by an empirically found relation. The transformation is assumed to only take place in the dominant transformation regions. A function bounded between 0 and 1 is mapped to the transformation region. Most often an exponential function or a cosine function is used for this purpose. The models of this type require knowledge on the history of the wire, making them more involved to implement. Additionally, the accuracy of the models is limited as transformation also occurs outside the dominant transformation regions.

A last modeling strategy is to use generally applicable hysteresis models. There are several of such models available. Note that not all are capable of modeling the hysteresis effect involved with SMA-actuators. In preferred embodiments of the invention, the computationally expensive operator-based models are disregarded. Alternative generic hysteresis models are the differential-based models, such as the Bouc-Wen model and the Jiles-Atherton model. These models can be written in a more general form (the Duhem model). For the Duhem model, specific describing functions are derived for modelling of the SMA behavior. Additionally, the Duhem model is invertible. Note that the Duhem model is a computationally cheap model. These properties make it an ideal model for the reference governor used in embodiment of the present invention.

The Duhem model and its inverse are used for the reference governor. The Duhem model ($\mathcal{H}$ in FIG. 4) describes the hysteresis behavior between manipulated input $w(t)=T(t)$ and output $z(t)$. We assume that the crystallographic fraction is equal to the scaled displacement. As a consequence, the output is equal to $z=\xi_n$ (non-detwinned fraction). The model, originally proposed by Dutta, uses a describing functions for the output at the major loop ($h_\pm$) and the slope of the major loop ($g_\pm$):

$$h_+ = \frac{1}{2}\left(1 + \mathrm{erf}\left(\frac{T-\mu_+}{\sqrt{2}\,\sigma_+}\right)\right), \quad \dot{T} > 0 \tag{3}$$

$$h_- = \frac{1}{2}\left(1 + \mathrm{erf}\left(\frac{T-\mu_-}{\sqrt{2}\,\sigma_-}\right)\right), \quad \dot{T} \leq 0 \tag{4}$$

$$g_\pm = \frac{\partial h_\pm}{\partial T} = \frac{1}{\sqrt{2\pi}\,\sigma_\pm}\exp\left(-\frac{(T-\mu_\pm)^2}{2\sigma_\pm^2}\right) \tag{5}$$

Note that the subscripts + and − denote the increasing and decreasing curve, respectively. The slope functions are defined by a Gaussian probability density function (PDF), with a mean $\mu_\pm$ and a standard deviation $\sigma_\pm$.

These describing functions, which are bounded, are used in the Duhem model to map a change in manipulated input to change in output:

$$\dot{\xi}_n = n_+(T, \xi)g_+(T)\dot{T}, \quad \dot{T} > 0 \tag{6}$$

$$\dot{\xi}_n = n_-(T, \xi)g_-(T)\dot{T}, \quad \dot{T} \leq 0 \tag{7}$$

$$n_+ = \max\left(0, \frac{h_-(T) - \xi_n}{h_-(T) - h_+(T)}\right) \tag{8}$$

$$n_- = \max\left(0, \frac{\xi_n - h_+(T)}{h_-(T) - h_+(T)}\right) \tag{9}$$

Note that $n_\pm$ are lower bounded by 0, as will be discussed later.

As clear from FIG. 4, an inverse $\mathcal{H}^{-1}$ of the Duhem model is used. As both $n_\pm$ and $g_\pm$ are independent of $\dot{T}$ and $\dot{\xi}_n$, the following reformulation is valid:

$$\dot{T} = \frac{\dot{\xi}_n}{n_+ g_+}, \quad \dot{\xi}_n > 0 \tag{10}$$

$$\dot{T} = \frac{\dot{\xi}_n}{n_- g_-}, \quad \dot{\xi}_n \leq 0 \tag{11}$$

Note that $n_+=0$ at the decreasing outer loop ($h_-$). Likewise, $n_-=0$ at the increasing outer loop. Hence, an unwanted devision by zero, and thus unfeasibly large rate of temperatures, can occur. As limitations on the rate of temperature are known, a straightforward solution is to bound the rate of temperature by the physical limitations. Hence, the inverse is $$\dot{T} = \min\left(\frac{\dot{\xi}_n}{n_+ g_+}, \dot{w}_{max}\right), \quad \dot{\xi}_n > 0 \tag{12}$$

$$\dot{T} = \max\left(\frac{\dot{\xi}_n}{n_- g_-}, \dot{w}_{min}\right), \quad \dot{\xi}_n \leq 0. \tag{13}$$

Note that $\dot{w}_{min,max}$ are the limited rate of temperature as defined in Eq. 1.

As implementation of the reference governor is in discrete time, also the (inversed) Duhem model is also rewritten in discrete time. First, for simplicity, an explicit Euler solution is derived from Eq. 6 and Eq. 7:

$$\xi_{n_{k+1}} = \xi_{n_k} + n_+(T_k, \xi_{n_k})(h_+(T_{k+1}) - h_+(T_k)), \quad T_{k+1} - T_k > 0 \tag{14}$$

$$\xi_{n_{k+1}} = \xi_{n_k} + n_-(T_k, \xi_{n_k})(h_-(T_{k+1}) - h_-(T_k)), \quad T_{k+1} - T_k \leq 0 \tag{15}$$

Here k denotes the sample number.

Similarly, the inverse Duhem model can be formulated as follows:

$$T_{k+1} = \min\left(h_+^{-1}\left(h_+(T_k) + \frac{\xi_{n_{k+1}} - \xi_{n_k}}{n_+(T_k, \xi_{n_k})}\right), T_k + \Delta T_{kmax}\right), \tag{16}$$

$$\xi_{n_{k+1}} - \xi_{n_k} > 0$$

-continued $$T_{k+1} = \max\left(h_-^{-1}\left(h_-(T_k) + \frac{\xi_{n_{k|1}} - \xi_{n_k}}{n_-(T_k, \xi_{n_k})}\right), T_k + \Delta T_{kmin}\right), \quad (17)$$

$$\xi_{n_{k+1}} - \xi_{n_k} \leq 0$$

with $$h_\pm^{-1} = \left(\sqrt{2}\,\sigma_\pm \text{erf}^{-1}(2\xi_n - 1)\right) + \mu_\pm \quad (18)$$

Note that the functions $h_\pm^{-1}$ are the functional inverses of the functions $h_\pm$. Thus, $h_\pm^{-1}$ describe the temperature as a function of fraction ($0 \leq \xi_n \leq 1$) during the major loop. Likewise, Eq. 18 denotes the functional inverse of the Gauss error function. Note that the argument q for $h_\pm^{-1}(q)$ is bounded to $q \in (0, 1)$. Identification of the temperature model, as well as derivation of the bounds on the rate of temperature $\Delta T_{k\ min,max}$ are treated below.

Figure 6:
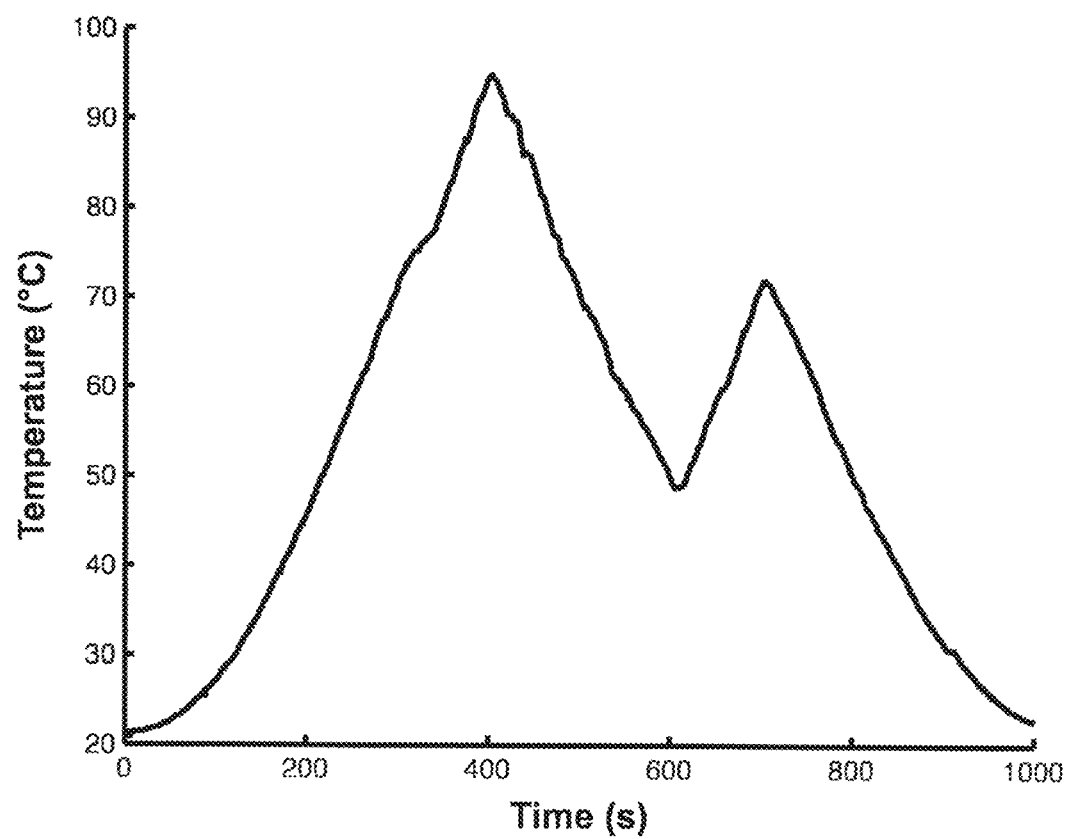
FIG. 6 is a graph of temperature vs. time showing a temperature profile of manipulated input (w=T) used for identification of the (inverse) Duhem model. It is designed such that both an outer loop and an inner loop is included.

The parameters of the Duhem model $\mu_\pm$, $\sigma_\pm$ can be identified in an optimal sense by minimization of the cost function for an sufficiently exciting estimation data-set $$J_D = \min_{\mu_\pm, \sigma_\pm} \sum_{k=1}^{N-1} (z_k^m - z_k)^2, \quad (19)$$

where $z_k^m$ is the measured displacement and $z_k$ is the estimated output. For identification purposes, the input is chosen such that the temperature profile in FIG. 6 is achieved.

Figure 7:
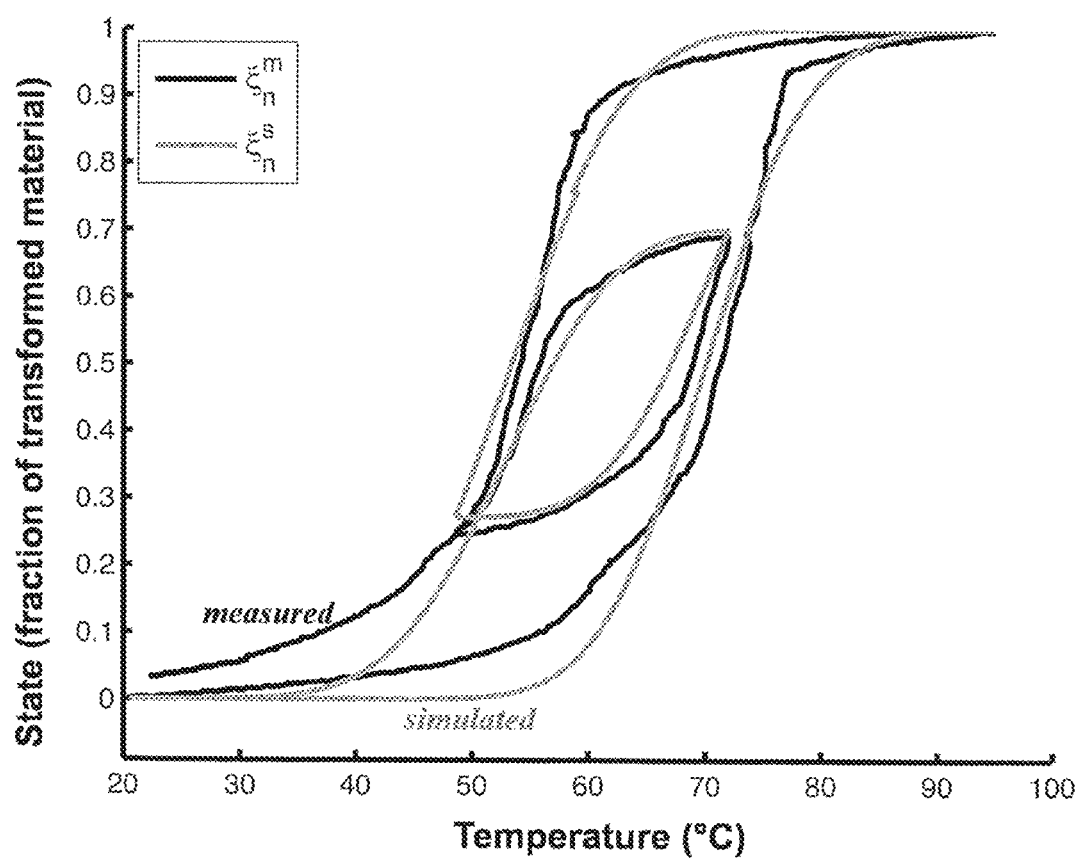
FIG. 7 is a graph of system state vs. temperature, showing the response of the Duhem hysteresis model, combined with the fraction during measurement, corresponding with the manipulated input depicted in FIG. 6.

This input results in an outer loop (full transformation) and an inner loop (partial transformation). This behavior is depicted in FIG. 7.

The identified parameters are provided in Table 1.

TABLE 1

| Parameter | Value | Unit |
|---|---|---|
| $\mu_+$ | 335.4 | K |
| $\mu_-$ | 325.9 | K |
| $\sigma_+$ | 7.1 | K |
| $\sigma_-$ | 10.0 | K |

The corresponding simulated output $\xi_n^s$ is depicted in FIG. 7 (solid line) as well as measured output (dark solid line). The RMS error is $3.97 \cdot 10^{-2}$ and the peak error is $9.85 \cdot 10^{-2}$. Note that, especially for low fraction values, there is a mismatch between the modeled- and measured output. This mismatch is dominantly caused by the limitations of the describing functions. The symmetric functions do not fully capture the non-symmetric non-linear phenomena of SMA. Note that all of the hysteresis models discussed earlier suffer from this effect. As a consequence, it is possible that an initial point is obtained that is outside the outer loop of the model.

To be robust for points outside the outer loop, $n_\pm$ are defined as Eq. 8 Eq. 9, hence $n_\pm$ have a lower limit of 0. If this is not implemented, it becomes possible that a decrease in temperature results in an increase of fraction or visa versa. Hence, without the limitations, the model behavior outside the outer loop does not represent the physical behavior of SMA.

Figure 8:
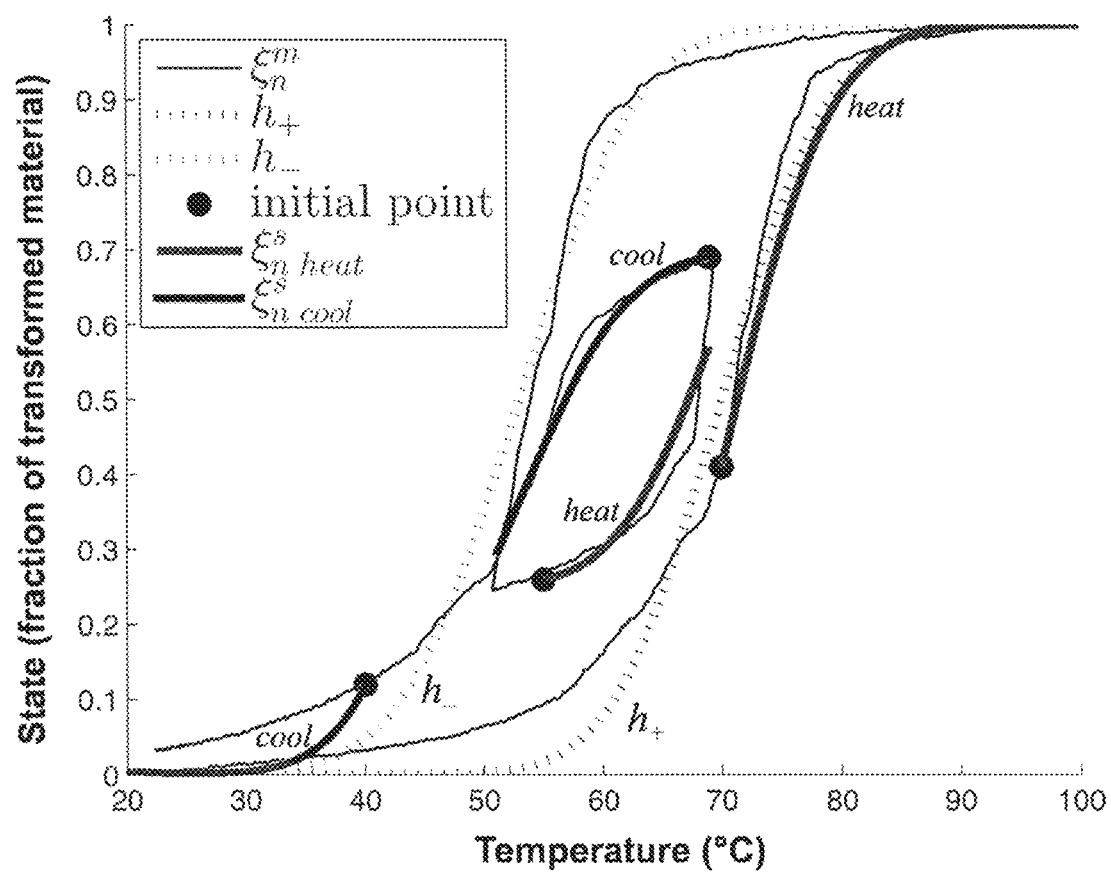
FIG. 8 is a graph of system state vs. temperature, where the outer loops ($h_±$) and the measured and simulated fraction are depicted. As initial state for the simulation, the black points are selected. Several are outside the outer loops, but the simulation result converges to the outer loop. Hence, the model is robust for situations where the states escape from the outer loop.

To check efficacy of the proposed limitations, initial points in- and outside the outer loops are investigated; model and simulation are compared. The result is depicted in FIG. 8.

For implementation of the reference governor approach, a temperature model is used ($\Delta w$ in FIG. 4). For example, balance of thermal energy can be used as a basis of the model. The thermal energy balance for cylindrical solid objects heated by Joule heating and cooled by natural convection is given by $$\dot{E} = \frac{d}{dt}(cmT) = E_h - E_c, \quad (20)$$

$$E_h = Ri^2, \quad (21)$$

$$E_c = \pi dL\beta(T - T_\infty), \quad (22)$$

where c is the specific heat coefficient, m is the mass of the wire, R is the electrical resistance of SMA, d is the wire diameter, L is the wire length, $\beta$ is the heat transfer coefficient and $T_\infty$ is the environment temperature. Note that m is constant over time. Additionally, for temperatures below 300 K, c is not dependent on the fraction of transformed material $\xi_d$. The first order system is discretized to allow implementation in the reference governor framework, resulting in the following model:

$$E_{k+1} = A_l E_k + B_l i^2, \quad (23)$$

$$T_k = T_\infty + C_l E_k, \quad (24)$$

where $A_l$, $B_l$ and $C_l$ are lumped parameters. In an attempt to address the fraction-dependency in the parameters, and thereby, further improve the temperature model, it is assumed that R, and d vary linearly with fraction, e.g., $R = R_n \xi_n + R_d \xi_d$, where the subscript denotes the material state. For instance, $R_d$ denotes the resistance for the material, when it is completely in detwinned martensite state. As a consequence of these fraction dependent parameters, some of the lumped parameters become fraction dependent:

$$A_l = A_n \xi_n + A_d \xi_d,\ B_l = B_n \xi_n + B_d \xi_d, C_l = 1/cm, \quad (25)$$

where c is the specific heat capacity and m is the mass.

Figure 9:
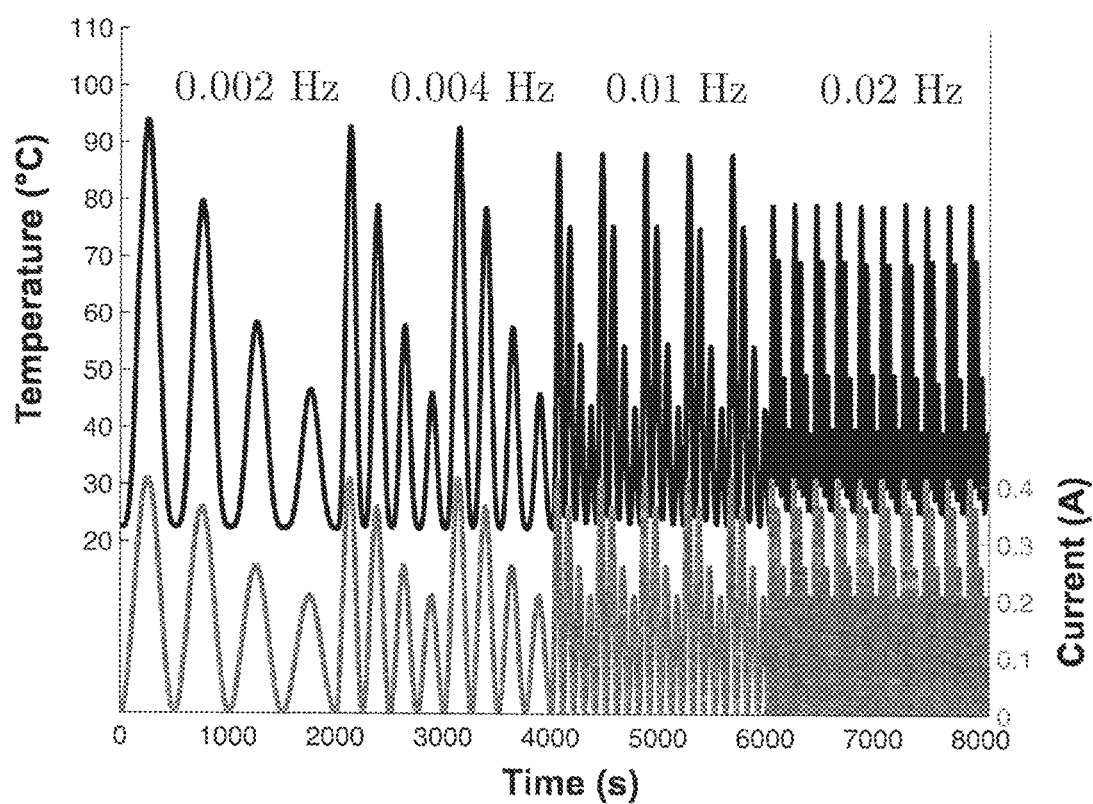
FIG. 9 is a graph of temperature and current-input measurements vs. time, which are used to identify the temperature model. The input is chosen such that both outer and inner loops occur in the response, additionally, several excitation frequencies are chosen to capture dynamical effects.
Figures 10A, 10B:
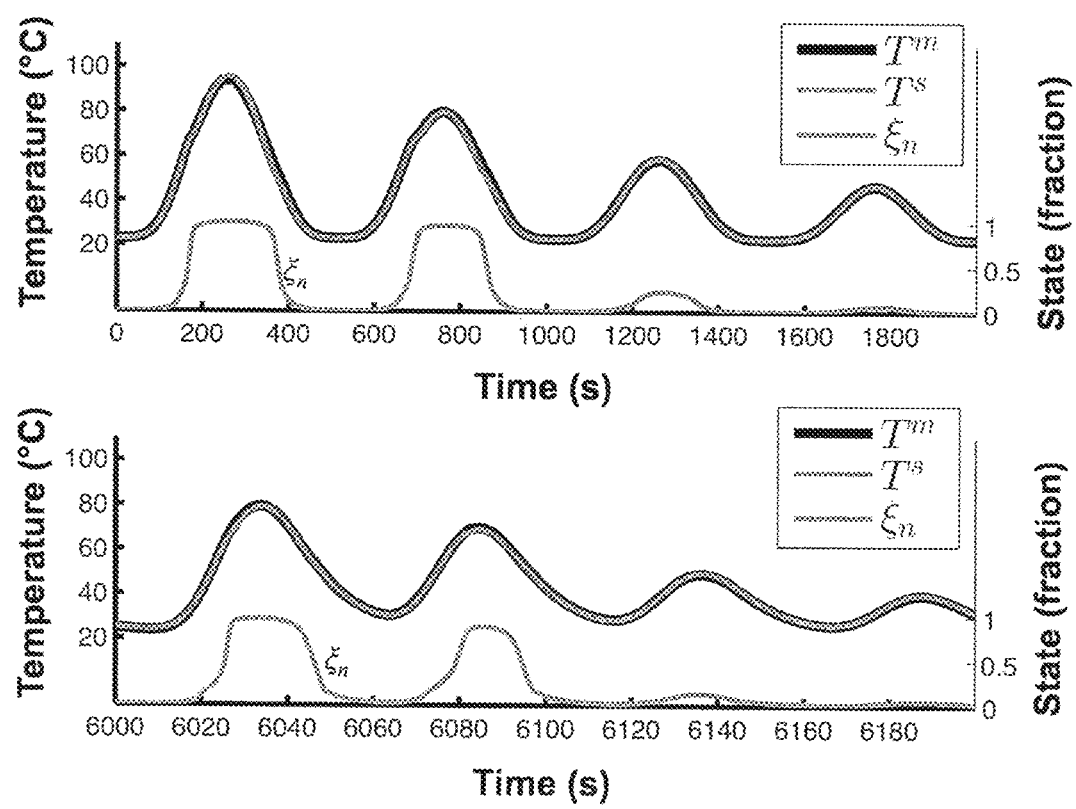
FIG. 10A and FIG. 10B are graphs of measured temperature, simulated temperature, and fraction of transformed material vs. time, illustrating identification measurements for the temperature model. The model is dependent on the fraction of transformed material ($\xi_d$).
Figure 11:
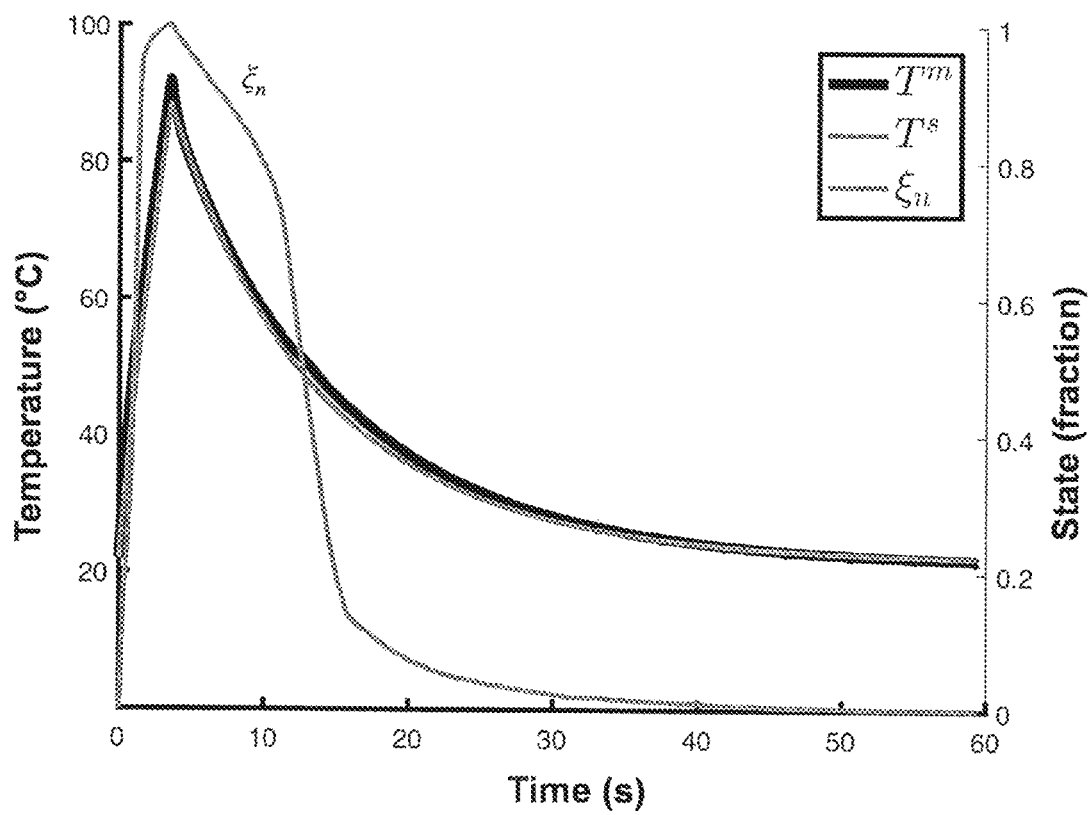
FIG. 11 is a graph of simulated and measured temperatures and state vs. time, illustrating validation measurements for the temperature model. The model is dependent on the fraction of transformed material ($\xi_d$).

Note that $A_{n,d}$, $B_{n,d}$ and $C_l$ are fully dependent on material properties and the sample time $t_s$, e.g., $B_{n,d} = R_{n,d} t_s$. The parameters of this model are identified by minimizing a cost function for a sufficiently exciting trajectory:

$$J_T = \min_{A_n, A_d, B_n, B_d, C_l} \sum_{k=1}^{N-1} (T_k^m - T_k)^2, \quad (26)$$

with N the number of data points and $T_k^m$ the measured temperature. The input contains decreasing sinusoids with an outer loop and several inner loops, this is depicted in FIG. 9. Note that this reference contains partial- and full-transformations and several excitation frequencies, it is selected as such to be able to identify both the dynamic- and the fraction-related-properties of the temperature dynamics. The measured temperature response and model output are depicted in the graphs of FIG. 10A and FIG. 10B, which represent the lowest and highest identification frequency, respectively. To validate the model, the SMA wire is heated by applying a current of 0.7 A for 3.5 s. After this time interval the current is removed and the wire cools down to the environment temperature. Both the measured and modeled temperature is depicted in FIG. 11.

It is concluded that the non-linear model proposed in Eq. 23-Eq. 25 accurately describes the temperature of the wire. An overview of the identified parameters is provided in Table 2.

TABLE 2

| Parameter | Value | Unit |
| --- | --- | --- |
| $A_n$ | $98.99 \cdot 10^{-2}$ | |
| $A_d$ | $99.12 \cdot 10^{-2}$ | |
| $R_n$ | 5.10 | $\Omega$ |
| $R_d$ | 6.00 | $\Omega$ |
| $C_l$ | $23.33 \cdot 10^{-2}$ | |

The limitations on rate of temperature can be derived from Eq. 23-Eq. 25 and are fraction dependent:

$$\Delta T_{k,min,max} = \left(\frac{\xi_{n_k}}{C_n} + \frac{\xi_{d_k}}{C_d}\right). \quad (27)$$

$$(T_k((A_n-1)C_n\xi_{n_k} + (A_d-1)C_d\xi_{d_k}) + i^2_{min,max}(B_n\xi_{n_k} + B_d\xi_{d_k})).$$

In Eq. 27 the minimum current $i_{min}=0$ A (no heating), the maximum current is due to power limitations of the amplifier and is equal to $i_{max}=0.7$ A.

Figure 12A:
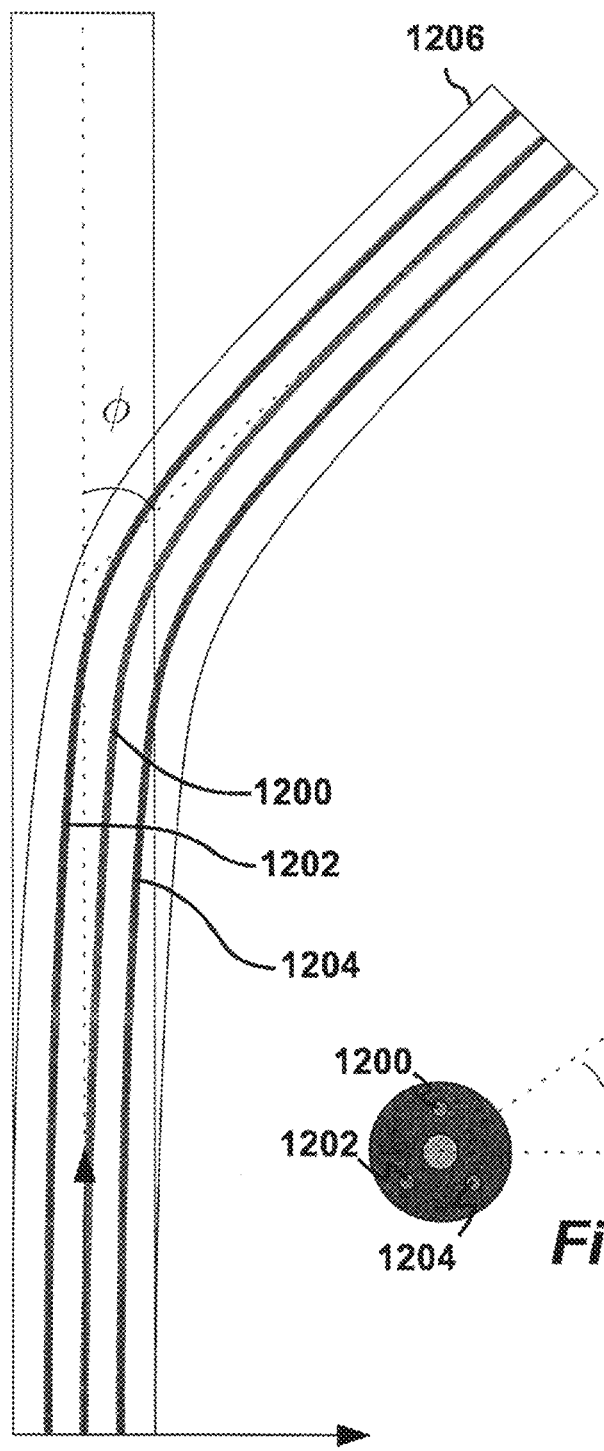
FIG. 12A and FIG. 12B are cross-sectional diagrams of an over-actuated catheter system with 3 SMA-actuator wires. The orientation of the catheter is described by the bending angle $\phi$ and the circumferential angle of direction $\theta$. This is considered the output of the catheter-system $z=[\phi\ \theta]^T$.
Figure 12B:
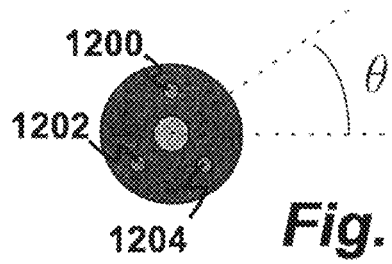

In one embodiment, a robotic SMA-actuated catheter is used to illustrate the efficacy of the reference governor for over-actuated systems. The catheter with SMA actuators 1200, 1202, 1204 for moving the tip 1206 is schematically illustrated in FIG. 12A and FIG. 12B. The output $z=[\phi \ \theta]^T$ in this embodiment has 2 angles, while there are 3 SMA actuators in the catheter, making the device over-actuated.

Like the bias-spring actuator, a linear relation between fraction and output is assumed. This is used to create a mapping of fractions of transformed material to an orientation of the catheter.

Figure 13:
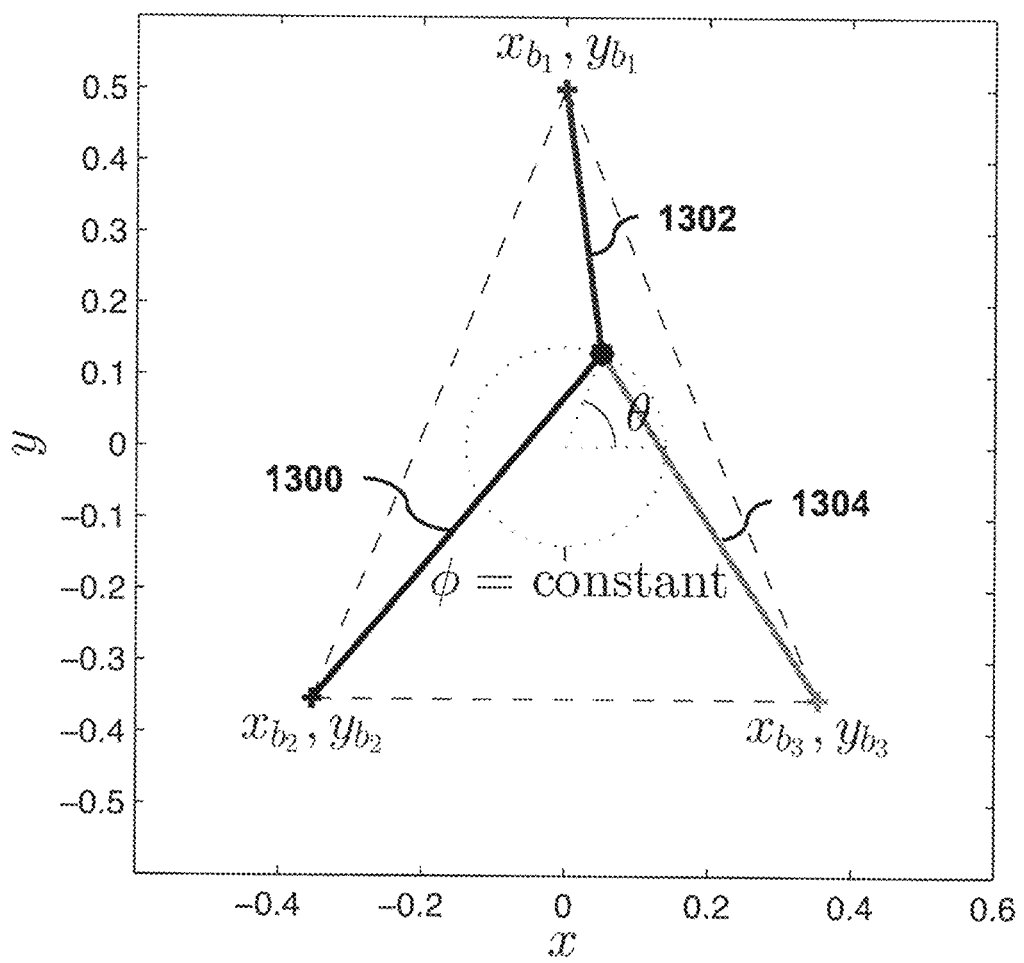
FIG. 13 is a graph of the mapping of 2D (x and y) to the orientation of the catheter [$\phi\ \theta$]. The solid lines denote the SMA-wires. Their scaled length relates to relative fraction of transformed material (relative to other wires). The mapping is allowed by assuming symmetry and a linear relation between fraction and output.

In FIG. 13, a 2D dotted triangle is depicted, in combination with a schematic illustration of 3 SMA wire actuators 1300, 1302, 1304 that are connected to a single point (the black dot). The wires are colored red, black and grey. The distance from the black dot to the origin of the coordinate system, relates to the bending angle $\phi$. Likewise, the circumferential angle of direction $\theta$, relates linear (with scaling factor K) to the circumferential angle around the origin:

$$\phi = K\sqrt{x^2 + y^2}, \quad (28)$$

$$\theta = \arctan\left(\frac{y}{x}\right). \quad (29)$$

It should be noted that x and y perform a mapping to differences in fraction among wires. As such, x and y do not relate directly to the length of the wires. The proposed mapping can assist in the initial guess for the fractions of the individual wires. The distance from corner i of the triangle $(x_{b_i}, y_{b_i})$ till the black cross (x, y) is between 0 and 1.

This distance can directly be related to a feasible fraction $\xi_{d_i,0}(=1\text{'}\xi_{n_i,0})$ of wire i;

$$\xi_{d_i,0} = \sqrt{(x-x_{b_i})^2 + (y-y_{b_i})^2}. \quad (30)$$

Note that an opposite statement does not hold in general; for instance the origin (x=0, y=0) corresponds to states where the fraction in all three wires is equal, however, not necessarily equal to $\xi_{d_{1,2,3}}=0.5$. The fact that several fraction combination result in identical output is resolved (and actively exploited) automatically during optimization in the reference governor. In order to relate the fractions of the wires $\xi_{d_i}$ to x and y, and thus to z, the following two equations are solved:

$$x = -\xi_{d_1}\sin(\tan^{-1}(v_1(x,y))) + \quad (31)$$
$$\xi_{d_2}\frac{\cos(\tan^{-1}(v_2(x,y)))}{\sqrt{2}} - \xi_{d_3}\frac{\cos(\tan^{-1}(v_3(x,y)))}{\sqrt{2}},$$

$$y = -\xi_{d_1}\cos(\tan^{-1}(v_1(x,y))) + \quad (32)$$
$$\xi_{d_2}\frac{\sin(\tan^{-1}(v_2(x,y)))}{\sqrt{2}} - \xi_{d_3}\frac{\sin(\tan^{-1}(v_3(x,y)))}{\sqrt{2}},$$

where $v_i$ is equal to $$v_i = \frac{x - x_{b_i}}{y - y_{b_i}}. \quad (33)$$

By applying the geometric rules Eq. 34 and Eq. 35 to Eq. 31 and Eq. 32, an equivalent formulation can be found as Eq. 36 and Eq. 37.

$$\sin(\tan^{-1}(q)) = \frac{q}{\sqrt{q^2+1}} \quad (34)$$

$$\cos(\tan^{-1}(q)) = \frac{1}{\sqrt{q^2+1}} \quad (35)$$

$$x = -\xi_{d_1}\frac{v_1(x,y)}{\sqrt{v_1(x,y)^2+1}} + \quad (36)$$
$$\xi_{d_2}\frac{1}{\sqrt{2(v_2(x,y)^2+1)}} - \xi_{d_3}\frac{1}{\sqrt{2(v_3(x,y)^2+1)}},$$

$$y = -\xi_{d_1}\frac{1}{\sqrt{v_1(x,y)^2+1}} + \quad (37)$$
$$\xi_{d_2}\frac{v_2(x,y)}{\sqrt{2(v_2(x,y)^2+1)}} - \xi_{d_3}\frac{v_3(x,y)}{\sqrt{2(v_3(x,y)^2+1)}}.$$

Note that Eq. 36 and Eq. 37 are two equations with two unknowns. This non linear set of equations is solved for x and y, in this case by using Powell's dog-leg algorithm. Hence, the fractions can be related back to the orientation of the catheter.

The approach discussed above is applied in experiments on a bias-spring actuator set-up, further, simulations are performed for the over-actuated catheter system. The sampling time of the set-up is equal to $t_{s,sys}=500$ Hz. In order to reduce computation time, the model and reference governor are sampled at $t_{s,RG}=10$ Hz and linear interpolation is applied.

Figure 14:
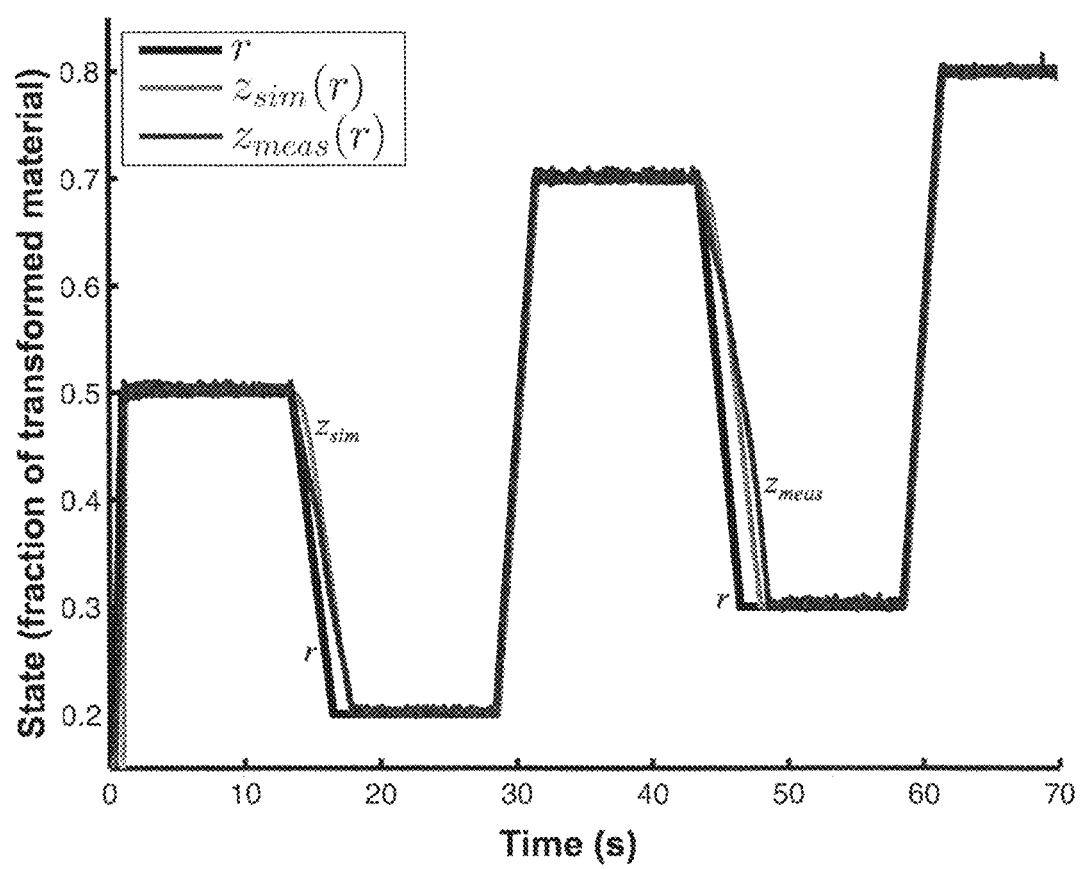
FIG. 14 is a graph of state for reference signal, simulated output, and measured output vs. time, illustrating a closed loop response of 1D bias-spring SMA-actuator (no RG), showing simulation results matching with output of the system.

A scanning reference signal is applied to the closed-loop system. The corresponding tracking results are depicted in FIG. 14. The grey line denotes the simulated output (based on the temperature- and Duhem model) and the red line corresponds to the measurements obtained during the closed-loop experiment.

Note that FIG. 14 is without using the reference governor.

Figure 15:
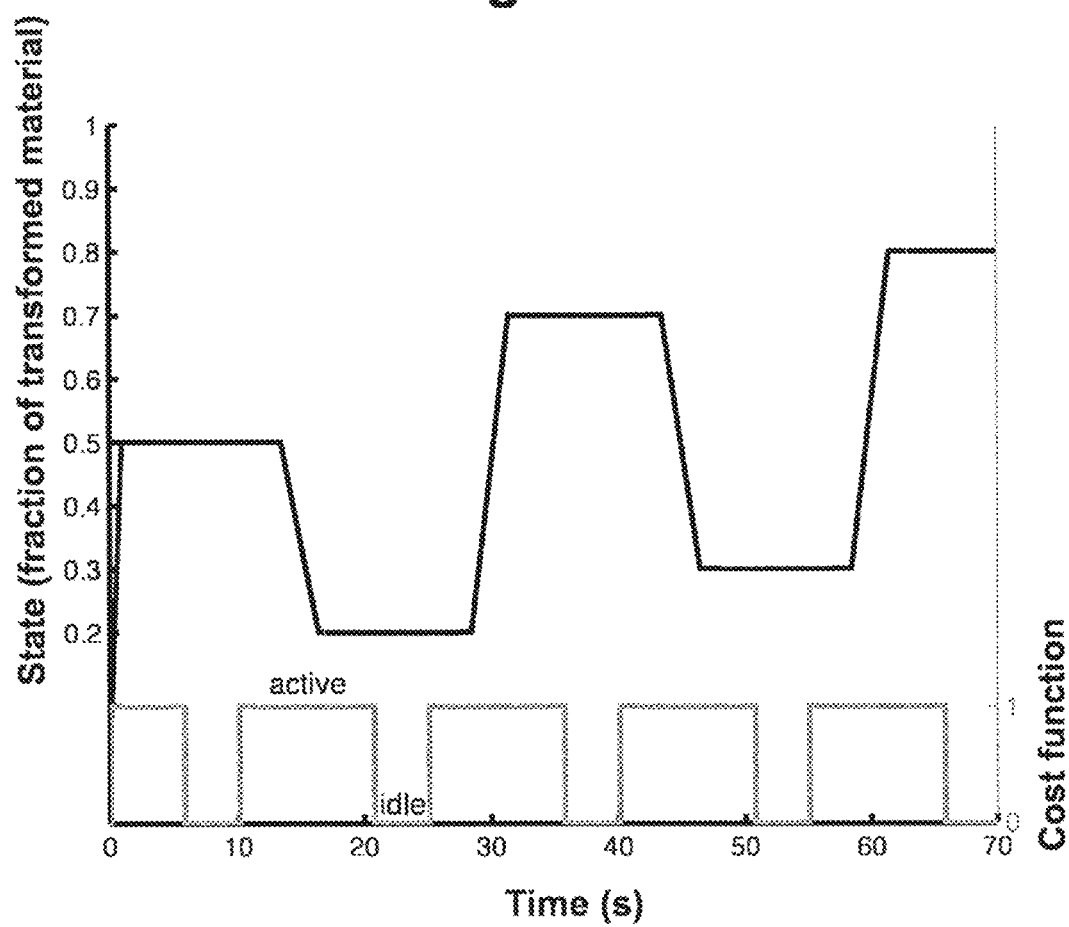
FIG. 15 is a graph of state and cost function vs. time, illustrating a scanning reference signal. It is assumed motion tracking is most important during the scanning movement. Therefore, the cost function Q (grey) is defined to provide an alternative cost function.

It is assumed that for the scanning motion tracking is important during the movement and a short period before and after the movement. Therefore, cost function Eq. 2 is altered to allow freedom in the remaining intervals. The latter prevents the optimizer from cutting off corners of the scanning trajectory. The new weighted cost function is defined as $$J_w = \min_{\hat{r}} \sum_{k=1}^{N-1} Q(r - \phi(\hat{r}))^2. \quad (38)$$

Where Q is a function that is 1 during active time and 0 during idle time; this is depicted in FIG. 15. Note that in ϕ, the (inverse) hysteresis model used ($\mathcal{H}^{(-1)}$) is the Duhem model.

Figure 16:
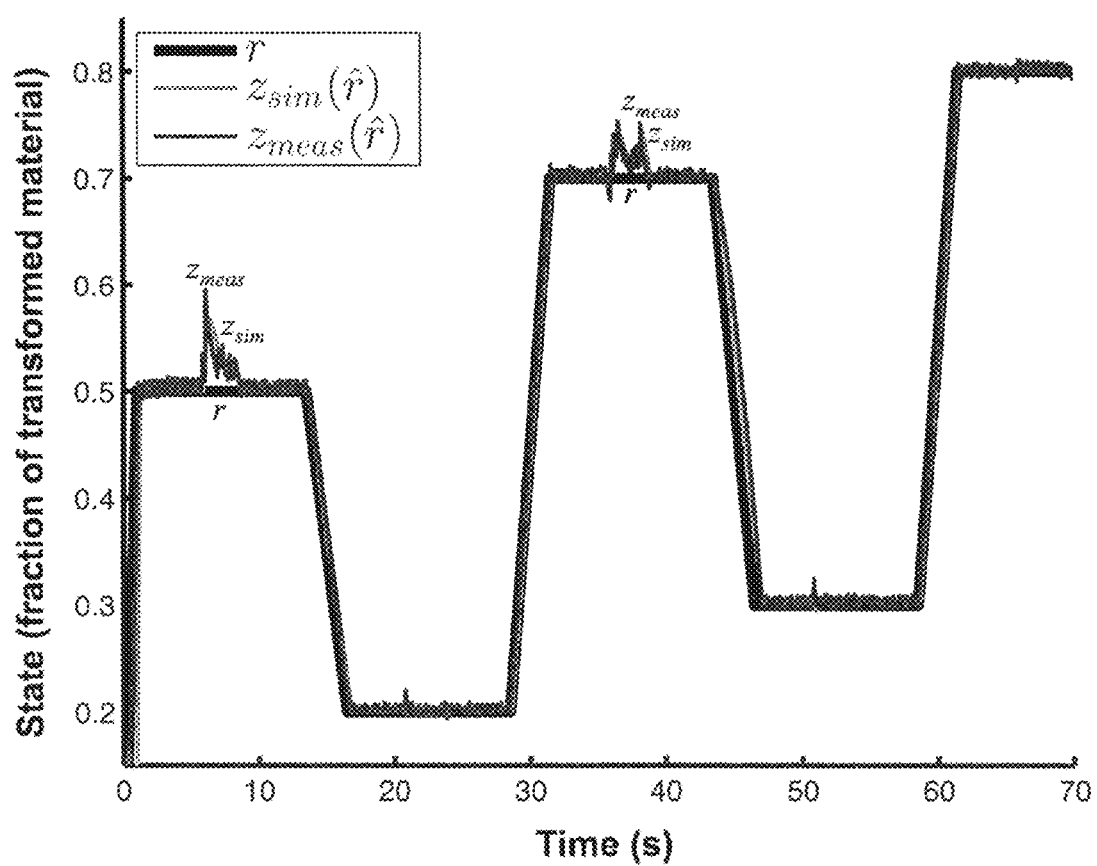
FIG. 16 is a graph of state for reference, simulated output and measured output vs. time, illustrating closed loop response of 1D bias-spring SMA-actuator (with RG), showing simulation results matching with output of the system.

When applying the reference governor using the proposed reference and cost function Eq. 38, the reference is altered to allow for improved tracking, especially in the case where the rate of change of the manipulated input is limited (limitations on cooling speed of the system). The tracking results for the proposed approach are depicted in FIG. 16, where the grey line denotes the simulated output (based on the temperature- and Duhem model) and the red line corresponds to the measurements obtained during the closed-loop experiment.

Figure 17:
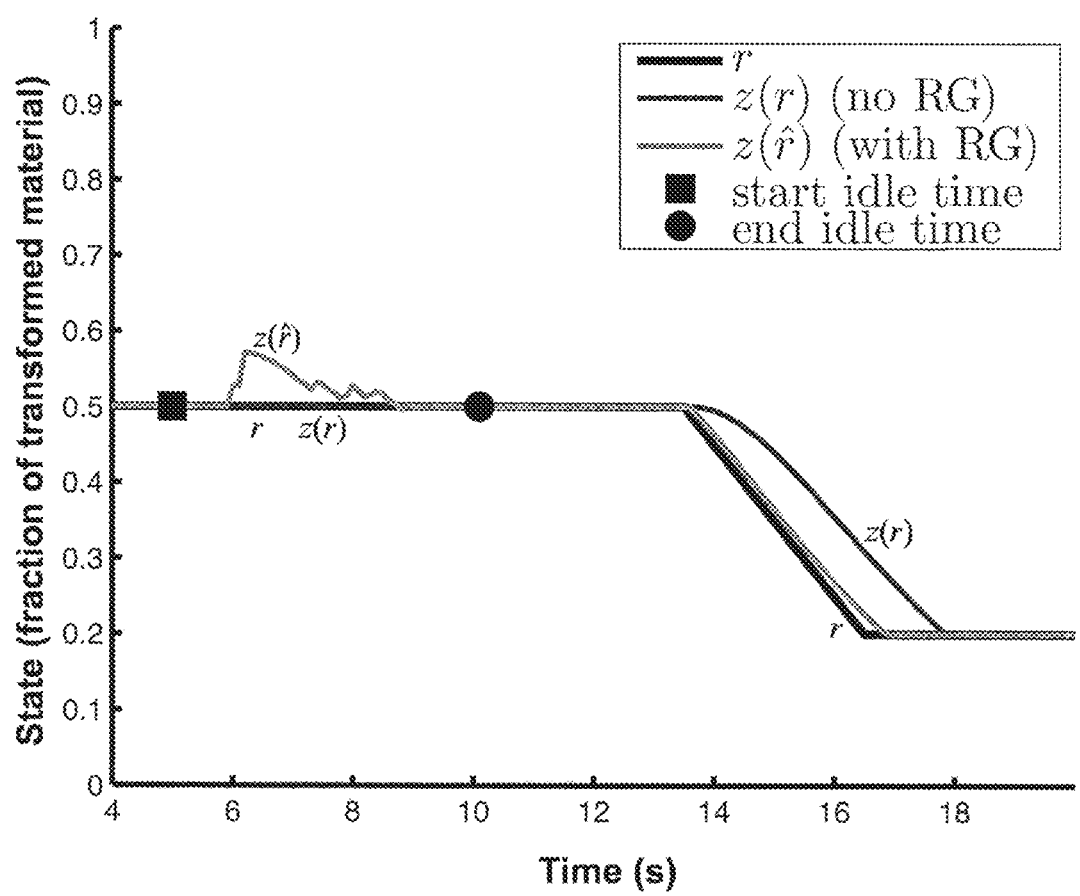
FIG. 17 is a graph of state for reference, output with RG and output without RG vs. time, illustrating how the control method modifies the signal when Q=0 (idle time); therefore at the end of the idle time (circle) the temperature is considerably lower compared to a classical control structure having no RG. As a consequence, from t=14 s, better tracking of the reference is obtained by the present control method. The hysteresis loop is depicted in FIG. 18.
Figure 18:
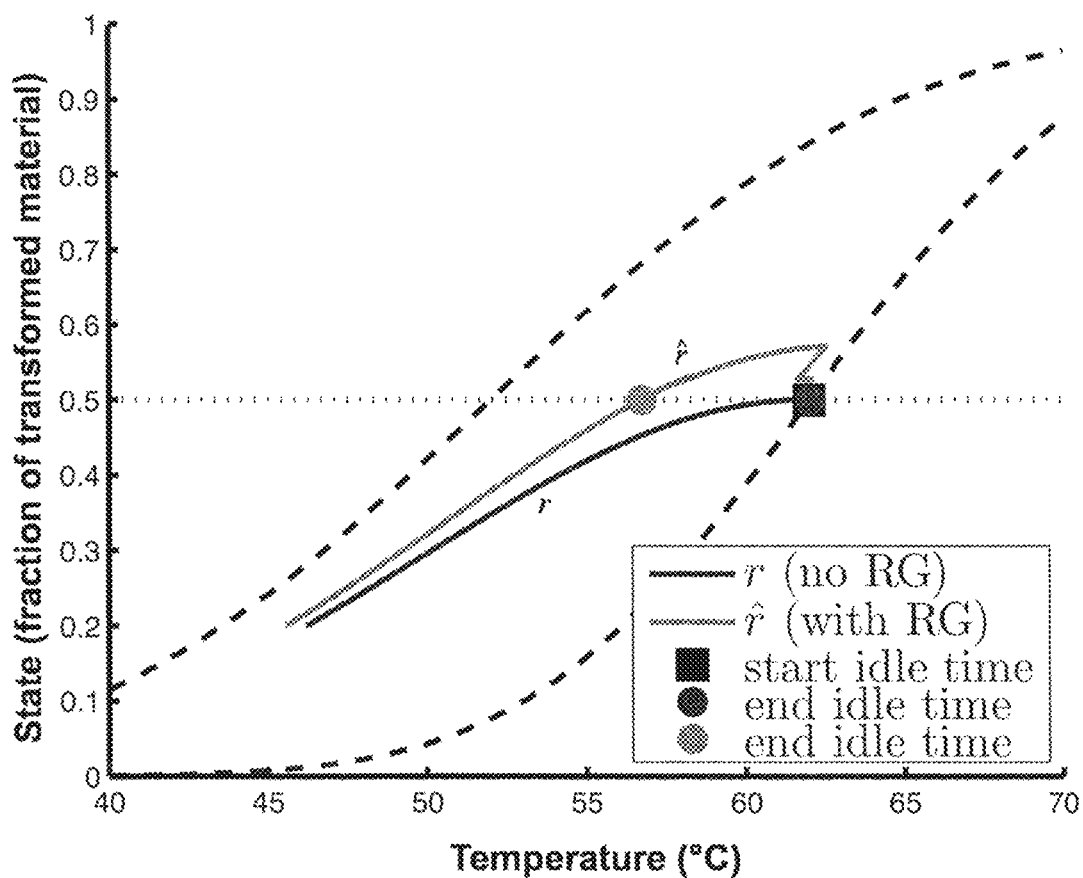
FIG. 18 is a graph of state vs. temperature, illustrating how the present method (with RG) modifies the signal when Q=0 (idle time); therefore at the end of the idle time (circle) the temperature is considerably lower compared to a classical control structure (without RG). As a consequence, from t=14 s, better tracking of the reference is obtained by the present control method. The corresponding time-response is depicted in FIG. 17.

The altered reference and the original reference are depicted in the same graph in FIG. 17. In FIG. 17, clearly between the square (start idle time) to the circle (end idle time) the system deviates from the original reference. As a consequence, significant tracking improvement is obtained elsewhere when a fraction decrease is required. This is visualized in FIG. 18, where the outer loops of the hysteresis curve are depicted as the dotted lines. With the altered reference, the system has an identical output at start and end of the idle time. However, the manipulated input state (temperature) is significantly dropped during this idle time. Hence, if afterwards a decrease of manipulated input is required to follow the reference, e.g., during 10-16 seconds, significantly less reduction in manipulated input is required. Since the rate of change is limited, this can result in faster actuation, thus in this case, better tracking. It should be noted that due to the zero-weighting in time interval 5.5-10 seconds, there is no unique solution of the optimization Eq. 38 for this interval, resulting in the non-smooth behavior of the simulated output.

The weighted least-squares tracking error is defined as Eq. 39. Where n is the output dimension (n=1 for the bias-spring actuator set-up) and N is the number of points in the data set. By applying the reference governor, the weighted least-squares tracking error is reduced; with 88% in simulation and 81% during experiments.

$$e_{LS} = \sum_{j=1}^{n} \left( \sum_{k=1}^{N} Q(k)(r_j(k) - z_j(k)) \right) \quad (39)$$

Note that in a general case without idle time, due to the slope at the inner loops, an increase of performance at a certain period in time results in a decrease of performance at another time. However, with an over-actuated system (more actuators than degrees of freedom), the benefits can be obtained without deteriorating performance at other times.

As an example, the reference governor is applied in simulation to an over-actuated catheter system. The system includes 3 SMA wires, which are placed off-centered at 120° angle from each-other, as depicted in FIG. 12. The wires are constructed inside a polymer tube with high axial stiffness. The SMA-wires are pre-stressed and are melted inside the tube. A change of length of a wire results in bending of the tube.

Figure 19:
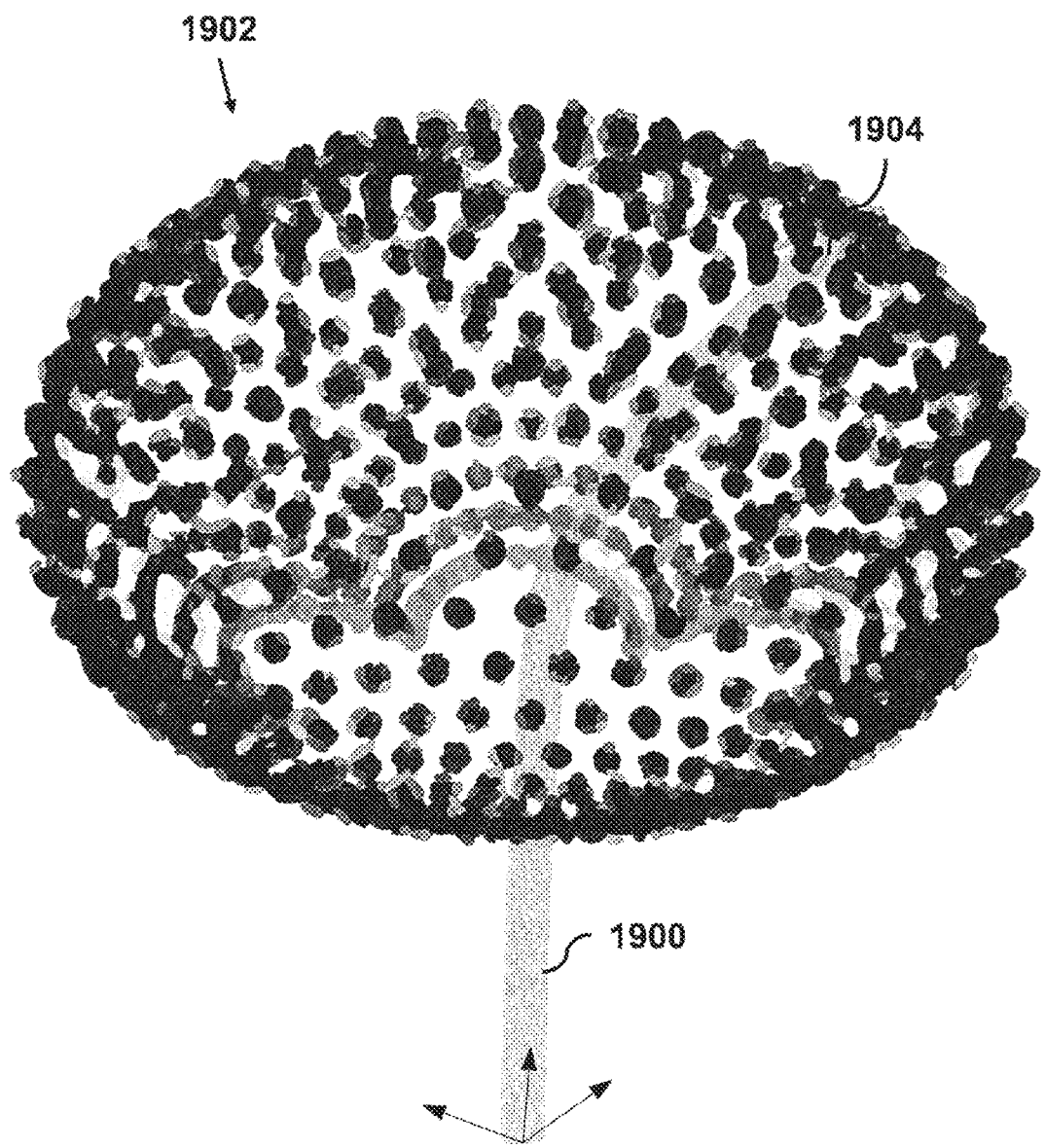
FIG. 19 is a perspective diagram of a final element method calculation illustrating tip positions (dots) for linearly distributed crystallographic fractions between 0 and 1 for each wire, forming a mushroom-shaped surface. Additionally, an arbitrary catheter orientation is shown.

A wire can be heated by applying current. It then will shrink, and the catheter will bend in the specific direction. By removing the current the catheter will go to its initial state. This can be made quicker by applying a current to the remaining wires and by that providing additional pulling force. Hence, the SMA wires are antagonists for other wires. As the axial stiffness of the catheter is high the total length of the catheter remains the same. Hence, the end effector (tip) 1904 of the catheter 1900 can move with 2 degrees of freedom on a mushroom-shaped surface 1902, as illustrated by results of FEM modeling in FIG. 19. The surface 1902 is formed by bending of the catheter in a certain direction, denoted ϕ and θ in FIG. 12. As a consequence, 3 SMA actuators result in a 2 dimensional output z=$[\phi \ \theta]^T$. Thus, the catheter is an over-actuated system.

To visualize the performance of the tracking accuracy, the surface is mapped to a plane. The details of this mapping (which have influence on $\mathcal{H}$ and $\mathcal{H}^{-1}$) were described above. A challenging reference trajectory is chosen and depicted in FIG. 20, the corresponding fraction reference signal r is obtained using Eq. 30.

Figure 20:
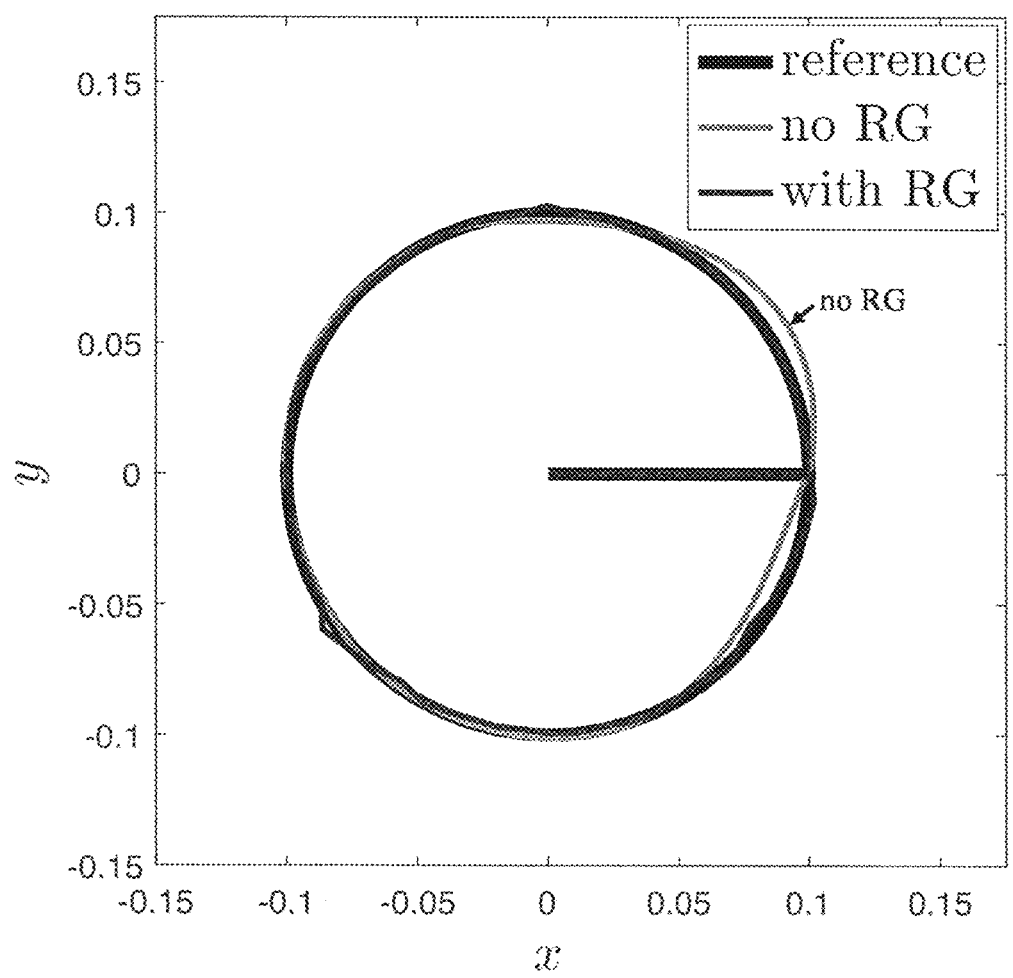
FIG. 20 is a graph of x-y tracking results and reference for the 2D mapped orientation of the catheter (see also FIG. 13). Response of the classic control structure (no RG) and the present method (with RG) are shown.
Figures 21A, 21B:
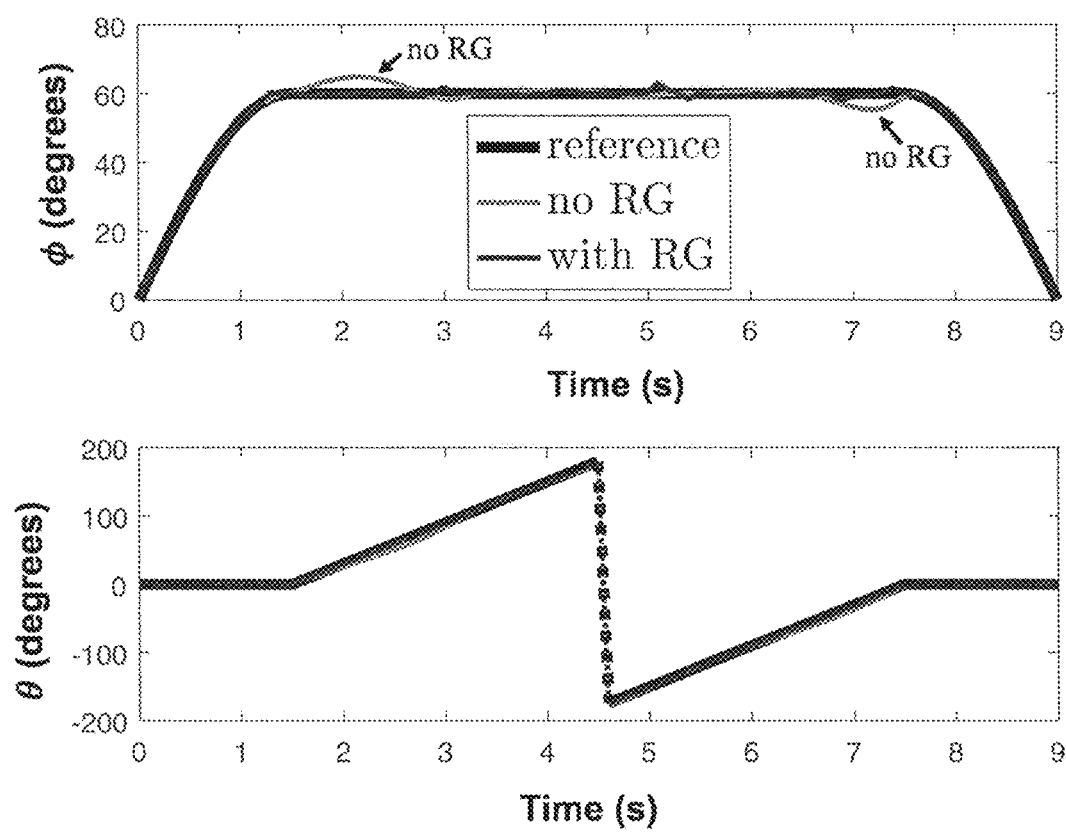
FIG. 21A and FIG. 21B are graphs of tracking results of $\phi$ and $\theta$, respectively, showing the reference, response of the classic control structure (without RG), and the present control method (with RG).

The simulated output with and without the reference governor is depicted in FIG. 20 and FIGS. 21A-B. The measure of tracking accuracy is defined as Eq. 39. The tracking error is reduced with 85% using the reference governor. Note that for an over-actuated system, no idle time or weighting is required (Q(k)=1 ∀k). Hence, superior performance is obtained over the complete trajectory. A speed versus accuracy trade-off can be made here, in this theoretical case, a slower trajectory could eliminate the error completely.

The device and control method of the present invention allows for exploiting of hysteretic effects in a system, allowing for faster actuation in case of input limitations.

In particular, the framework is experimentally demonstrated for SMA actuation in a catheter, although the principles are directly applicable to similar bendable tube devices such an endoscopes. The limited temperature rate in the considered SMA actuators, combined with the inherent hysteresis motivate the need of the proposed methodology.

Limitations on tracking accuracy in case of fast actuation are overcome. By allowing a performance loss at certain time intervals the least-squares tracking error is reduced by 88% in simulation and 81% during experiments. For over-actuated systems, no performance loss at alternative time-intervals are required. In particular, this is demonstrated by a simulation example of a robotic SMA-actuated catheter tip. For fast actuation of the SMA-actuated catheter system, tracking error is reduced by 85% using this control method.

The invention claimed is:

1. A method for controlling an over-actuated system having shape memory alloy (SMA) hysteretic wire actuators, the method comprising:
   (a) generating by a controller a control signal, wherein the control signal is generated based on a temperature model that takes into account physical limitations of the SMA hysteretic wire actuators, and a hysteresis model that describes hysteresis behavior of the SMA hysteretic wire actuators;
   (b) inputting to the SMA hysteretic wire actuators the control signal, wherein the SMA hysteretic wire actuators comprise at least three SMA wire actuators;

(c) changing displacement states of the SMA hysteretic wire actuators based on the control signal, such that a tip of the over-actuated system moves with a number of degrees of freedom less than the number of SMA wire actuators.

2. The method of claim 1 wherein the over-actuated system is a catheter.

3. The method of claim 1 wherein the tip of the over-actuated system moves with two degrees of freedom, and wherein the number of SMA wire actuators is at least three.

4. The method of claim 1 wherein the hysteresis model is the Duhem model.

5. The method of claim 1 wherein the controller comprises a feedback controller that tracks a reference signal representing a desired value of an output of the SMA hysteretic wire actuators.

6. The method of claim 1 wherein the controller comprises a reference governor that generates a smart reference signal from a reference signal representing a desired value of an output of the SMA hysteretic wire actuators.

7. The method of claim 6 wherein the smart reference signal minimizes an error between the reference signal and an achievable output.

8. The method of claim 6 wherein the control signal is generated based on the smart reference signal.

9. The method of claim 6 wherein the reference governor is dependent on the hysteresis model and an inverse hysteresis model.

10. An over-actuated device comprising:
(a) a bendable tube comprising at least three shape memory alloy (SMA) hysteretic wire actuators having displacement states that change in response to a control signal such that a tip of the over-actuated system moves with a number of degrees of freedom less than the number of SMA wire actuators;
(b) a controller connected to the bendable tube, wherein the controller generates a control signal and inputs the control signal to the SMA hysteretic wire actuators, wherein the control signal is generated by the controller based on a temperature model that takes into account physical limitations of the SMA hysteretic wire actuators, and a hysteresis model that describes hysteresis behavior of the SMA hysteretic wire actuators.

11. The device of claim 10 wherein the bendable tube is part of a catheter.

12. The device of claim 10 wherein the tip of the over-actuated system moves with two degrees of freedom, and wherein the number of SMA wire actuators is at least three.

13. The device of claim 10 wherein the hysteresis model is the Duhem model.

14. The device of claim 10 wherein the controller comprises a feedback controller that tracks a reference signal representing a desired value of an output of the SMA hysteretic wire actuators.

15. The device of claim 10 wherein the controller comprises a reference governor that generates a smart reference signal from a reference signal representing a desired value of an output of the SMA hysteretic wire actuators.

* * * * *